(12) United States Patent
Zhou et al.

(10) Patent No.: US 11,986,673 B2
(45) Date of Patent: May 21, 2024

(54) SYSTEMS AND METHODS FOR GENERATING RADIATION TREATMENT PLAN

(71) Applicant: SHANGHAI UNITED IMAGING HEALTHCARE CO., LTD., Shanghai (CN)

(72) Inventors: Jingjie Zhou, Shanghai (CN); Li Wang, Shanghai (CN); Cheng Ni, Shanghai (CN); Johannes Stahl, Houston, TX (US); Jonathan Maltz, Houston, TX (US)

(73) Assignee: SHANGHAI UNITED IMAGING HEALTHCARE CO., LTD., Shanghai (CN)

( * ) Notice: Subject to any disclaimer, the term of this patent is extended or adjusted under 35 U.S.C. 154(b) by 351 days.

(21) Appl. No.: 17/443,453

(22) Filed: Jul. 26, 2021

(65) Prior Publication Data
US 2021/0353963 A1 Nov. 18, 2021

Related U.S. Application Data

(63) Continuation of application No. 16/109,707, filed on Aug. 22, 2018, now Pat. No. 11,071,877, which is a (Continued)

(51) Int. Cl.
*A61N 5/10* (2006.01)

(52) U.S. Cl.
CPC .......... *A61N 5/1047* (2013.01); *A61N 5/1031* (2013.01); *A61N 5/1045* (2013.01);
(Continued)

(58) Field of Classification Search
CPC .... A61N 2005/1032; A61N 2005/1034; A61N 2005/1035; A61N 5/1031; A61N 5/1036;
(Continued)

(56) References Cited

U.S. PATENT DOCUMENTS

| 5,548,627 A | 8/1996 | Swerdloff et al. |
| 5,754,623 A | 5/1998 | Seki |

(Continued)

FOREIGN PATENT DOCUMENTS

| CN | 101422640 A | 5/2009 |
| CN | 102184330 A | 9/2011 |

(Continued)

OTHER PUBLICATIONS

International Search Report in PCT/CN2018/085279 dated Jan. 23, 2019, 5 Pages.

(Continued)

*Primary Examiner* — Chih-Cheng Kao
(74) *Attorney, Agent, or Firm* — METIS IP LLC

(57) ABSTRACT

A method for generating a radiation treatment plan is provided. The method may include determining a set of one or more optimization goals for radiation delivery by a therapeutic radiation delivery apparatus. The method may also include determining a plan for radiation delivery from a radiation source of the therapeutic radiation delivery apparatus. The radiation source may be capable of continuously rotating around a subject. The plan may include a plurality of radiation segments. Each radiation segment may be characterized by at least one parameter selected from a start angle, a stop angle, a two-dimensional segment shape, or a segment MU value such that the plurality of radiation segments satisfy the set of one or more optimization goals by superimposing at least two radiation segments from at least two different rotations into a target volume of the subject.

17 Claims, 15 Drawing Sheets

Related U.S. Application Data continuation of application No. PCT/CN2018/085279, filed on May 2, 2018.

(52) U.S. Cl.
CPC .... *A61N 5/1081* (2013.01); *A61N 2005/1032* (2013.01); *A61N 2005/1034* (2013.01); *A61N 2005/1035* (2013.01); *A61N 5/1036* (2013.01); *A61N 5/1039* (2013.01)

(58) Field of Classification Search
CPC .. A61N 5/1039; A61N 5/1045; A61N 5/1081; A61N 5/103; A61N 5/104
See application file for complete search history.

(56) References Cited

U.S. PATENT DOCUMENTS

| | | | |
|---|---|---|---|
| 5,818,902 A | | 10/1998 | Yu |
| 6,459,762 B1 | * | 10/2002 | Wong ............. A61N 5/10 378/65 |
| 8,340,247 B2 | | 12/2012 | Keall et al. |
| 10,478,138 B2 | | 11/2019 | Tian et al. |
| 2003/0086530 A1 | | 5/2003 | Otto |
| 2005/0152495 A1 | | 7/2005 | Hesse |
| 2006/0067469 A1 | | 3/2006 | Dooley et al. |
| 2006/0256915 A1 | | 11/2006 | Otto et al. |
| 2007/0016014 A1 | | 1/2007 | Hara et al. |
| 2009/0225942 A1 | | 9/2009 | Shepard et al. |
| 2009/0251709 A1 | | 10/2009 | Kindlein |
| 2010/0202588 A1 | | 8/2010 | Shibuya et al. |
| 2010/0208274 A1 | | 8/2010 | Kindlein et al. |
| 2010/0219356 A1 | * | 9/2010 | Bzdusek ........ A61N 5/1047 378/65 |
| 2011/0186755 A1 | | 8/2011 | Otto |
| 2011/0235860 A1 | | 9/2011 | Keall et al. |
| 2012/0008744 A1 | | 1/2012 | Bani-Hashemi |
| 2012/0123184 A1 | * | 5/2012 | Otto ............... A61N 5/1067 600/1 |
| 2013/0301893 A1 | | 11/2013 | Netsch et al. |
| 2015/0141733 A1 | | 5/2015 | Kumar et al. |
| 2016/0271423 A1 | | 9/2016 | Takahashi |
| 2018/0078789 A1 | | 3/2018 | Ollila et al. |
| 2019/0099144 A1 | | 4/2019 | Rieger et al. |
| 2019/0168025 A1 | | 6/2019 | Koponen et al. |
| 2020/0030633 A1 | | 1/2020 | Van Heteren et al. |
| 2020/0164225 A1 | * | 5/2020 | Zhang ............. A61N 5/1031 |

FOREIGN PATENT DOCUMENTS

| | | |
|---|---|---|
| CN | 107982646 A | 5/2018 |
| CN | 110432920 A | 11/2019 |
| CN | 209630457 U | 11/2019 |
| CN | 110917509 A | 3/2020 |
| WO | 2016000777 A1 | 1/2016 |
| WO | 2017174625 A1 | 10/2017 |
| WO | 2018031365 A1 | 2/2018 |
| WO | 2019210455 A1 | 11/2019 |

OTHER PUBLICATIONS

Written Opinion in PCT/CN2018/085279 dated Jan. 23, 2019, 5 Pages.

International Search Report in PCT/CN2018/085266 dated Jan. 30, 2019, 5 Pages.

Written Opinion in PCT/CN2018/085266 dated Jan. 30, 2019, 3 Pages.

\* cited by examiner

SYSTEMS AND METHODS FOR GENERATING RADIATION TREATMENT PLAN

CROSS-REFERENCE TO RELATED APPLICATIONS

This present application is a continuation of U.S. application Ser. No. 16/109,707, filed on Aug. 22, 2018, which is a continuation of International Application No. PCT/CN2018/085279, filed on May 2, 2018, the contents of each of which are hereby incorporated by reference.

TECHNICAL FIELD

The present disclosure generally relates to radiation therapy, and more specifically relates to systems and methods for generating a radiation treatment plan of a radiation therapy delivered by a therapeutic radiation delivery apparatus including a treatment radiation source rotatable at a relatively high rotation speed.

BACKGROUND

Radiation therapy has been widely employed in cancer therapy by directing ionizing radiation towards a tumor. Considerations of radiation therapy include that the tumor receives sufficient radiation and that damage to an organ at risk (OAR) is minimized as much as possible during the radiation therapy. The tumor and/or the OAR may be in motion due to a physiological motion (e.g., respiratory motion, cardiac motion, muscle contraction and relaxation). In image-guided radiation therapy (IGRT), three-dimensional (3D) or two-dimensional (2D) imaging (or 2D/3D imaging with time) can be used to localize the tumor and/or detect tumor motion.

SUMMARY

In one aspect of the present disclosure, a method is provided. The method may be implemented on at least one machine each of which has at least one processor and at least one storage device for determining a radiation treatment plan. The method may include determining a set of one or more optimization goals for radiation delivery by a therapeutic radiation delivery apparatus. The method may also include determining a plan for radiation delivery from a radiation source of the therapeutic radiation delivery apparatus. The radiation source may be capable of continuously rotating around a subject. The plan may include a plurality of radiation segments. Each radiation segment may be characterized by at least one parameter selected from a start angle, a stop angle, a two-dimensional segment shape, or a segment MU value such that the plurality of radiation segments satisfy the set of one or more optimization goals by superimposing at least two radiation segments from at least two different rotations into a target volume of the subject.

In another aspect of the present disclosure, a system is provided. The system may include at least one storage device storing a set of instructions and at least one processor in communication with the at least one storage medium. When executing the set of instructions, the at least one processor may be configured to cause the system to determine a set of one or more optimization goals for radiation delivery by a therapeutic radiation delivery apparatus. The at least one processor may be also configured to cause the system to determine a plan for radiation delivery from a radiation source of the therapeutic radiation delivery apparatus. The radiation source may be capable of continuously rotating around a subject. The plan may include a plurality of radiation segments. Each radiation segment may be characterized by at least one parameter selected from a start angle, a stop angle, a two-dimensional segment shape, or a segment MU value such that the plurality of radiation segments satisfy the set of one or more optimization goals by superimposing at least two radiation segments from at least two different rotations into a target volume of the subject.

In yet another aspect of the present disclosure, a non-transitory computer-readable medium is provided. The non-transitory computer-readable medium may include at least one set of instructions. When executed by at least one processor of a computing device, the at least one set of instructions may cause the at least one processor to effectuate a method including determining a set of one or more optimization goals for radiation delivery by a therapeutic radiation delivery apparatus. The at least one set of instructions may further cause the at least one processor to effectuate a method including determining a plan for radiation delivery from a radiation source of the therapeutic radiation delivery apparatus. The radiation source may be capable of continuously rotating around a subject. The plan may include a plurality of radiation segments. Each radiation segment may be characterized by at least one parameter selected from a start angle, a stop angle, a two-dimensional segment shape, or a segment MU value such that the plurality of radiation segments satisfy the set of one or more optimization goals by superimposing at least two radiation segments from at least two different rotations into a target volume of the subject.

In yet another aspect of the present disclosure, a method is provided. The method may be implemented on at least one machine each of which has at least one processor and at least one storage device for determining a radiation treatment plan. The method may include determining a set of one or more optimization goals for radiation delivery by a therapeutic radiation delivery apparatus. The method may also include determining a plurality of radiation segments by iteratively optimizing a dose distribution relative to the set of one or more optimization goals. The method may further include determining a sequence of the plurality of radiation segments for radiation delivery to obtain a delivery trajectory of a radiation source of the therapeutic radiation delivery apparatus. The method may further include determining the radiation treatment plan based on the plurality of sequential radiation segments for radiation delivery and the delivery trajectory of the radiation source of the therapeutic radiation delivery apparatus.

In yet another aspect of the present disclosure, a system is provided. The system may include at least one storage device storing a set of instructions and at least one processor in communication with the at least one storage medium. When executing the set of instructions, the at least one processor may be configured to cause the system to determine a set of one or more optimization goals for radiation delivery by a therapeutic radiation delivery apparatus. The at least one processor may be also configured to cause the system to determine a plurality of radiation segments by iteratively optimizing a dose distribution relative to the set of one or more optimization goals. The at least one processor may be also configured to cause the system to determine a sequence of the plurality of radiation segments for radiation delivery to obtain a delivery trajectory of a radiation source of the therapeutic radiation delivery apparatus. The at least one processor may be further configured to cause the system to determine the radiation treatment plan based on the plurality of sequential radiation segments for radiation delivery and the delivery trajectory of the radiation source of the therapeutic radiation delivery apparatus.

In yet another aspect of the present disclosure, a non-transitory computer-readable medium is provided. The non-transitory computer-readable medium may include at least one set of instructions. When executed by at least one processor of a computing device, the at least one set of instructions may cause the at least one processor to effectuate a method including determining a set of one or more optimization goals for radiation delivery by a therapeutic radiation delivery apparatus. The at least one set of instructions may also cause the at least one processor to effectuate a method including determining a plurality of radiation segments by iteratively optimizing a dose distribution relative to the set of one or more optimization goals. The at least one set of instructions may also cause the at least one processor to effectuate a method including determining a sequence of the plurality of radiation segments for radiation delivery to obtain a delivery trajectory of a radiation source of the therapeutic radiation delivery apparatus. The at least one set of instructions may further cause the at least one processor to effectuate a method including determining the radiation treatment plan based on the plurality of sequential radiation segments for radiation delivery and the delivery trajectory of the radiation source of the therapeutic radiation delivery apparatus.

In yet another aspect of the present disclosure, a method is provided. The method may be implemented on at least one machine each of which has at least one processor and at least one storage device for determining a radiation treatment plan. The method may include obtaining a set of one or more optimization goals for radiation delivery by a therapeutic radiation delivery apparatus and obtaining one or more imaging protocols that are to be executed during radiation therapy. The method may also include determining one or more radiation delivery parameters associated with the radiation treatment plan by iteratively optimizing a dose distribution relative to the set of one or more optimization goals. The radiation treatment plan may include a 3D imaging plan associated with the one or more imaging protocols to be executed during the radiation therapy.

In yet another aspect of the present disclosure, a system is provided. The system may include at least one storage device storing a set of instructions and at least one processor in communication with the at least one storage medium. When executing the set of instructions, the at least one processor may be configured to cause the system to obtain a set of one or more optimization goals for radiation delivery by a therapeutic radiation delivery apparatus and obtain one or more imaging protocols that are to be executed during radiation therapy. The at least one processor may be configured to cause the system to determine one or more radiation delivery parameters associated with the radiation treatment plan by iteratively optimizing a dose distribution relative to the set of one or more optimization goals. The radiation treatment plan may include a 3D imaging plan associated with the one or more imaging protocols to be executed during the radiation therapy.

In yet another aspect of the present disclosure, a non-transitory computer-readable medium is provided. The non-transitory computer-readable medium may include at least one set of instructions. When executed by at least one processor of a computing device, the at least one set of instructions may cause the at least one processor to effectuate a method including obtaining a set of one or more optimization goals for radiation delivery by a therapeutic radiation delivery apparatus and obtaining one or more imaging protocols that are to be executed during radiation therapy. The at least one set of instructions may also cause the at least one processor to effectuate a method including determining one or more radiation delivery parameters associated with the radiation treatment plan by iteratively optimizing a dose distribution relative to the set of one or more optimization goals. The radiation treatment plan may include a 3D imaging plan associated with the one or more imaging protocols to be executed during the radiation therapy.

In yet another aspect of the present disclosure, a method is provided. The method may be implemented on at least one machine each of which has at least one processor and at least one storage device for determining a radiation treatment plan. The method may include obtaining a radiation treatment plan including a delivery trajectory of a radiation source of a therapeutic radiation delivery apparatus and obtaining one or more imaging protocols that are to be executed during radiation therapy. The method may also include adjusting the radiation treatment plan based on the one or more imaging protocols and delivering a treatment radiation beam by the radiation source to the target volume according to the adjusted radiation treatment plan. The adjusted radiation treatment plan may include a 3D imaging plan associated with the one or more imaging protocols to be executed during the radiation therapy.

In yet another aspect of the present disclosure, a system is provided. The system may include at least one storage device storing a set of instructions and at least one processor in communication with the at least one storage medium. When executing the set of instructions, the at least one processor may be configured to cause the system to obtain a radiation treatment plan including a delivery trajectory of a radiation source of a therapeutic radiation delivery apparatus and obtain one or more imaging protocols that are to be executed during radiation therapy. The at least one processor may be configured to cause the system to adjust the radiation treatment plan based on the one or more imaging protocols and deliver a treatment radiation beam by the radiation source to the target volume according to the adjusted radiation treatment plan. The adjusted radiation treatment plan may include a 3D imaging plan associated with the one or more imaging protocols to be executed during the radiation therapy.

In yet another aspect of the present disclosure, a non-transitory computer-readable medium is provided. The non-transitory computer-readable medium may include at least one set of instructions. When executed by at least one processor of a computing device, the at least one set of instructions may cause the at least one processor to effectuate a method including obtaining a radiation treatment plan including a delivery trajectory of a radiation source of a therapeutic radiation delivery apparatus and obtaining one or more imaging protocols that are to be executed during radiation therapy. The at least one set of instructions may also cause the at least one processor to effectuate a method including adjusting the radiation treatment plan based on the one or more imaging protocols and delivering a treatment radiation beam by the radiation source to the target volume according to the adjusted radiation treatment plan. The adjusted radiation treatment plan may include a 3D imaging plan associated with the one or more imaging protocols to be executed during the radiation therapy.

Additional features will be set forth in part in the description which follows, and in part will become apparent to those skilled in the art upon examination of the following and the accompanying drawings or may be learned by production or operation of the examples. The features of the present disclosure may be realized and attained by practice or use of various aspects of the methodologies, instrumentalities and combinations set forth in the detailed examples discussed below.

BRIEF DESCRIPTION OF THE DRAWINGS

The present disclosure is further described in terms of exemplary embodiments. These exemplary embodiments are described in detail with reference to the drawings. The drawings are not to scale. These embodiments are non-limiting exemplary embodiments, in which like reference numerals represent similar structures throughout the several views of the drawings, and wherein.

DETAILED DESCRIPTION

In the following detailed description, numerous specific details are set forth by way of examples in order to provide a thorough understanding of the relevant disclosure. However, it should be apparent to those skilled in the art that the present disclosure may be practiced without such details. In other instances, well known methods, procedures, systems, components, and/or circuitry have been described at a relatively high-level, without detail, in order to avoid unnecessarily obscuring aspects of the present disclosure. Various modifications to the disclosed embodiments will be readily apparent to those skilled in the art, and the general principles defined herein may be applied to other embodiments and applications without departing from the spirit and scope of the present disclosure. Thus, the present disclosure is not limited to the embodiments shown, but to be accorded the widest scope consistent with the claims.

The terminology used herein is for the purpose of describing particular example embodiments only and is not intended to be limiting. As used herein, the singular forms "a," "an," and "the" may be intended to include the plural forms as well, unless the context clearly indicates otherwise. It will be further understood that the terms "comprise," "comprises," and/or "comprising," "include," "includes," and/or "including," when used in this specification, specify the presence of stated features, integers, steps, operations, elements, and/or components, but do not preclude the presence or addition of one or more other features, integers, steps, operations, elements, components, and/or groups thereof.

It will be understood that the term "system," "unit," "module," and/or "block" used herein are one method to distinguish different components, elements, parts, section or assembly of different level in ascending order. However, the terms may be displaced by other expression if they achieve the same purpose.

Figure 2:
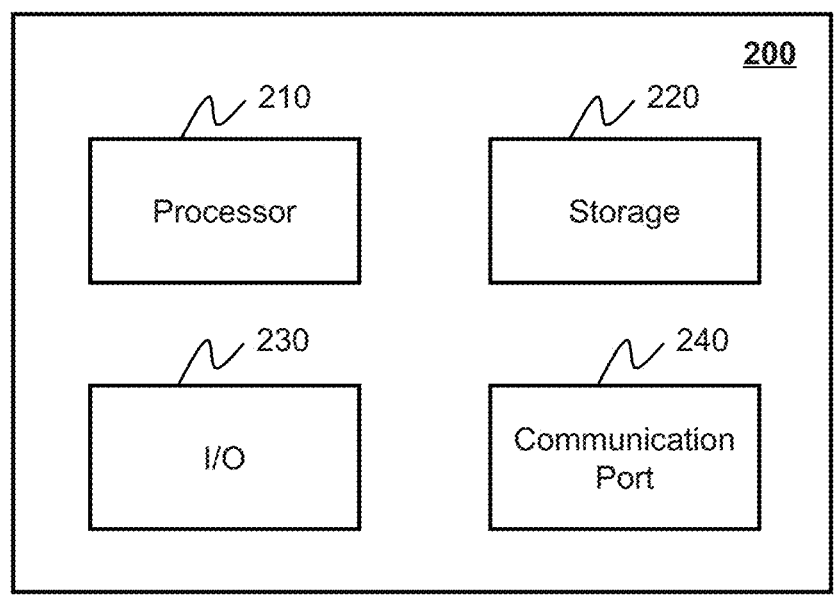
FIG. 2 is a schematic diagram illustrating exemplary hardware and/or software components of a computing device on which the processing device may be implemented according to some embodiments of the present disclosure.

Generally, the word "module," "unit," or "block," as used herein, refers to logic embodied in hardware or firmware, or to a collection of software instructions. A module, a unit, or a block described herein may be implemented as software and/or hardware and may be stored in any type of non-transitory computer-readable medium or other storage device. In some embodiments, a software module/unit/block may be compiled and linked into an executable program. It will be appreciated that software modules can be callable from other modules/units/blocks or from themselves, and/or may be invoked in response to detected events or interrupts. Software modules/units/blocks configured for execution on computing devices (e.g., processor 210 as illustrated in FIG. 2) may be provided on a computer readable medium, such as a compact disc, a digital video disc, a flash drive, a magnetic disc, or any other tangible medium, or as a digital download (and can be originally stored in a compressed or installable format that needs installation, decompression, or decryption prior to execution). Such software code may be stored, partially or fully, on a storage device of the executing computing device, for execution by the computing device. Software instructions may be embedded in a firmware, such as an EPROM. It will be further appreciated that hardware modules/units/blocks may be included of connected logic components, such as gates and flip-flops, and/or can be included of programmable units, such as programmable gate arrays or processors. The modules/units/blocks or computing device functionality described herein may be implemented as software modules/units/blocks, but may be represented in hardware or firmware. In general, the modules/units/blocks described herein refer to logical modules/units/blocks that may be combined with other modules/units/blocks or divided into sub-modules/sub-units/sub-blocks despite their physical organization or storage.

It will be understood that when a unit, engine, module or block is referred to as being "on," "connected to," or "coupled to," another unit, engine, module, or block, it may be directly on, connected or coupled to, or communicate with the other unit, engine, module, or block, or an intervening unit, engine, module, or block may be present, unless the context clearly indicates otherwise. As used herein, the term "and/or" includes any and all combinations of one or more of the associated listed items.

These and other features, and characteristics of the present disclosure, as well as the methods of operation and functions of the related elements of structure and the combination of parts and economies of manufacture, may become more apparent upon consideration of the following description with reference to the accompanying drawings, all of which form a part of this disclosure. It is to be expressly understood, however, that the drawings are for the purpose of illustration and description only and are not intended to limit the scope of the present disclosure. It is understood that the drawings are not to scale.

An aspect of the present disclosure relates to systems and methods for generating a radiation treatment plan. The radiation treatment plan may be suitable for a radiation therapy delivered by a therapeutic radiation delivery apparatus including a treatment radiation source rotatable at a relatively high rotation speed. To determine the radiation treatment plan, the systems and methods may obtain a set of one or more optimization goals for radiation delivery by a therapeutic radiation delivery apparatus. The systems and methods may determine a plurality of radiation segments by iteratively optimizing a dose distribution relative to the set of one or more optimization goals. Each of the plurality of radiation segments may be specified based on an angle range, one or more beam radiation types, one or more segment shapes, one or more beam energies, one or more segment MU values, or the like, or a combination thereof. The systems and methods may further determine a sequence of the plurality of radiation segments for radiation delivery to obtain a delivery trajectory of the radiation source. The radiation treatment plan may then be determined or generated.

In conventional treatment planning, for a static treatment technique, a treatment segment may correspond to a treatment delivery system configuration. One or more of a beam energy, a gantry position, a collimator position, a radiation field shape, and a radiation output (also referred to as MU value) may be specified. For a dynamic treatment technique, one or more parameters such as gantry angle, collimator angle, and radiation field shape may change during radiation delivery. A treatment segment may include a start gantry position and an end gantry position, a start collimator position and an end collimator position, and a start radiation field shape and an end radiation field shape, etc. In such cases, in a contemporary radiation therapy, a segment is delivered as it has been planned once per treatment session. In a standard multi-fraction treatment course, a particular segment may usually be delivered once on each treatment day, unless the treatment plan (prescription) is changed by a clinician. In the present disclosure, there are one or more possible interpretations of the term "segment." A first interpretation is "planning segment," which is used to characterize the radiation projected toward a target volume at the planning stage for dose calculation and plan optimization purposes. A second interpretation is "delivery segment," which is used to specify the machine delivery trajectory. A delivery segment may usually be delivered once on each fraction. In some embodiments of the present disclosure, the treatment plan is optimized with parameters (e.g., parameters related to one or more different interleaving patterns, distribution of radiation delivery over multiple rotations, and/or the number of rotations) as either prospectively-chosen or optimizable parameters. In such embodiments, a "planning segment" may be identical to a "delivery segment," in that the segments that are planned are intended to be delivered as optimized, with only the order of delivery being possibly determined at a later time (e.g., during treatment, subject to the current respiration state of a patient).

In some embodiments of the present disclosure, the treatment plan may be optimized without necessarily considering of the number of rotations and/or interleaving and/or overlapping parameters. After optimization, one "planning segments" may be decomposed into a number of overlapping and/or interleaved "delivery segments" to be delivered over multiple rotations without changing the accumulative dosimetric result of the previous planning segments (perhaps even during delivery, e.g., based on the patient respiration state or dosimetric feedback).

Figure 1:
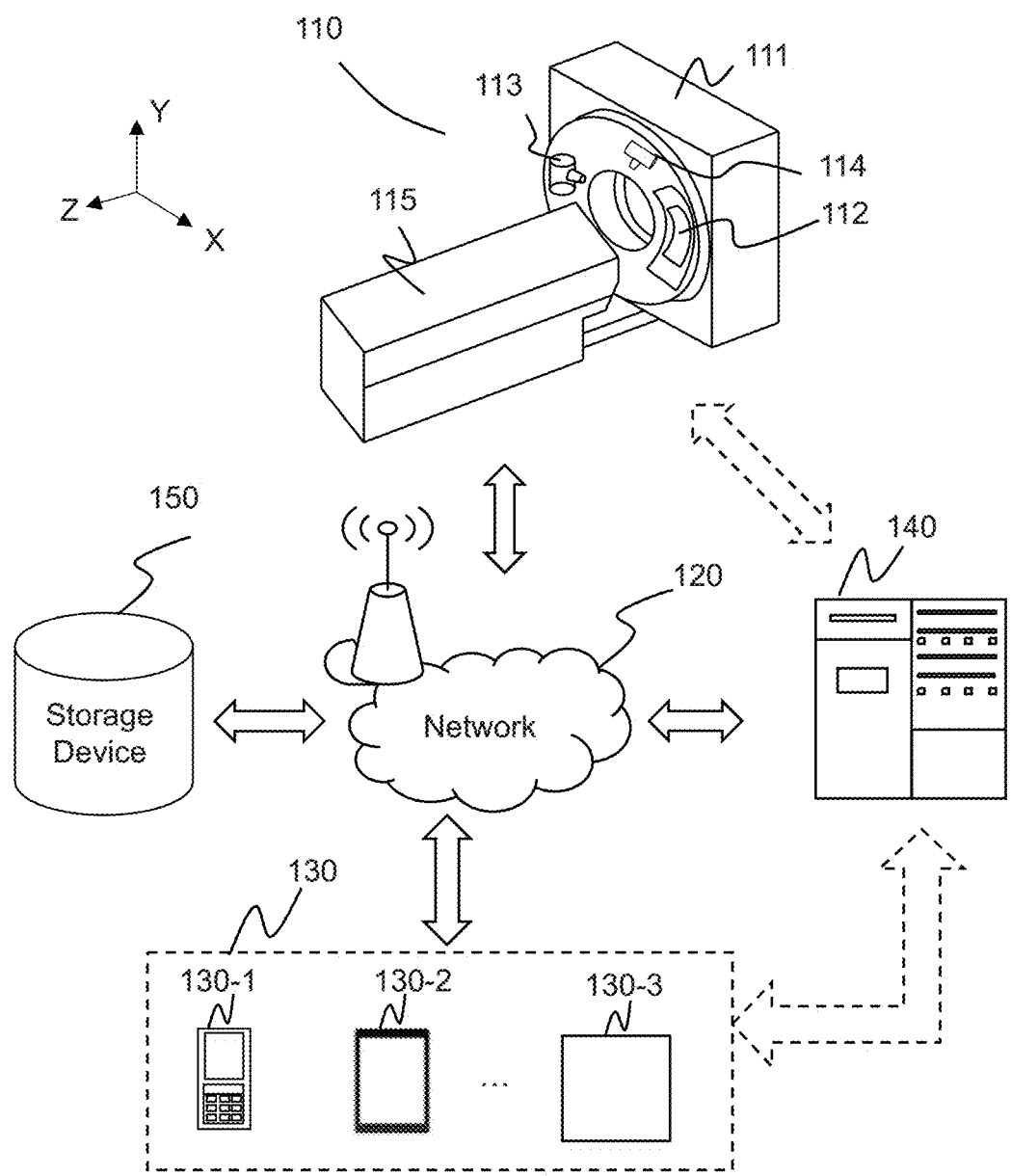
FIG. 1 is a schematic diagram illustrating an exemplary radiation system according to some embodiments of the present disclosure.

FIG. 1 is a schematic diagram illustrating an exemplary radiation system according to some embodiments of the present disclosure. As illustrated, the radiation system 100 may include a therapeutic radiation delivery apparatus 110, a network 120, one or more terminals 130, a processing device 140, and a storage device 150. The components in the radiation system 100 may be connected in one or more of various ways. Merely by way of example, the therapeutic radiation delivery apparatus 110 may be connected to the processing device 140 through the network 120. As another example, the therapeutic radiation delivery apparatus 110 may be connected to the processing device 140 directly as indicated by the bi-directional arrow in dotted lines linking the therapeutic radiation delivery apparatus 110 and the processing device 140. As a further example, the storage device 150 may be connected to the processing device 140 directly or through the network 120. As still a further example, the terminal 130 may be connected to the processing device 140 directly (as indicated by the bi-directional arrow in dotted lines linking the terminal 130 and the processing device 140) or through the network 120.

The therapeutic radiation delivery apparatus 110 may include an imaging assembly, a first or treatment radiation source 114, a gantry 111, and a table 115. The imaging assembly may include a conventional CT, a cone beam CT (CBCT), a helical CT, a multi-slice CT, a PET-CT or the like, or any combination thereof. The imaging assembly may be configured to generate one or more images before, during or after the radiation therapy. As shown in FIG. 1, the imaging assembly may include a second or imaging radiation source 113 (e.g., an X-ray tube) and a detector module 112. The gantry 111 may include a rotary ring (not shown in FIG. 1). The rotary ring may be configured to accommodate the second radiation source 113, the detector module 112, and the first radiation source 114. A subject may be placed on the table 115 and be moved along a Z-axis direction. The subject may be a biological subject (e.g., a patient, an animal) or a non-biological subject (e.g., a human-made subject). In the present disclosure, "subject" and "object" are used interchangeably.

Key to the teachings contained herein may be the concept of a cone beam X-ray imaging system, and cone beam computed tomography (CBCT). In the vast majority of X-ray imaging systems, X-rays may be produced by a Bremsstrahlung process in which electrons are incident on an X-ray target. The electrons may lose kinetic energy in the target, and this energy may be converted to heat and X-rays. X-rays may be emitted in all directions. In reflection targets (such as those used in the vast majority of diagnostic X-ray imaging systems), the X-rays emitted in the direction of the target may be substantially absorbed by the target. The X-rays that leave the target may be emitted over a wide solid angle. These rays usually leave the X-ray tube through an exit window that is substantially transparent to X-rays. If the exit window is circular, the shape of the beam may be a true cone. However, most systems (e.g., in planar radiography applications) may collimate the beam to a rectangular cross section. Nevertheless, such a beam may be also termed a cone beam. In single slice CT systems, the cone beam may be much more narrowly collimated along the long axis of the patient (direction that patient couch travels) than lateral axis (usually along the plane of rotation of the imaging system). Such a beam may be typically referred to as a fan beam, rather than a cone beam, even though the beam may, before collimation, have assumed the form of a cone. In multislice CT (and helical scan implementations of multislice CT), the detector typically may have larger axial extent than in the fan beam CTs. However, it is not typical to refer to the beam of a multislice CT as a cone beam, since it is much more substantially collimated in the axial direction as compared to the lateral direction.

Linear accelerator X-ray sources (e.g., the first radiation source 114 and the second radiation source 113) almost universally rely on Bremsstrahlung from transmission targets to generate photon beams. Like reflection sources, transmission targets may also generate X-rays that travel in all directions. However, the target may be itself substantially transparent to the emerging X-rays. The higher the energy of the incident electrons, the more concentrated is the flux of photons in the forward (transmission) direction (directions more closely aligned with that of the original electron beam). The emerging photon beams may be almost always collimated by a conical primary collimator, forming substantially a cone beam. However, this cone beam may be further collimated. In most systems, collimation may be achieved by rectangular jaws and/or a 2D multileaf collimator. In the present disclosure, such further collimated beams are also termed cone beams. In contrast, a minority of radiation therapy systems, such as that described in U.S. Pat. No. 5,548,627 (which describes the basis of the tomotherapy line of radiation therapy systems), are designed to produce a beam "only within the gantry plane." The gantry plane in such systems may be substantially narrower than the lateral extent of the patient and the treatment field. This narrow collimation along the long axis of the patient, by analogy with the fan beam CT and multislice CT cases, means that such a beam is not considered a cone beam by people having ordinary skills in the art of x-ray imaging and therapy systems. In fan beam CT, multislice CT, and tomotherapy, the patient support may be almost always translated along the long axis of the patient in order to image and/or treat all volumes of interest. In cone beam CT, and therapy with 2D (collimated) cone beams, the patient support may be almost never moved to accomplish imaging and/or treatment of volumes of interest.

In view of the above, the term "cone angle" as applied to a collimated cone beam, is taken to be the angle subtended at the source of the collimated beam, by the edges of the collimated field, in the particular direction along with the field is collimated. Understanding of the teachings contained herein require the disambiguation of the concept of a "CT detector" (e.g., the detector module 112). For CBCT, flat panel detectors may be normally used. These detectors may almost always have a relatively large area (e.g. 8 in×8 in, 16×16 in, 40 cm×30 cm), and low aspect ratio (ratios of length to width such as 1:1 and 4:3). In contrast, CT detectors may not be flat, and may have much higher aspect ratios, where the arc length of the detector in the plane of rotation (lateral extent, or fan angle) greatly exceeds the axial dimension (and subjected axial angle from the source) of the detector. In most cases, CT detectors may be arranged along an isocentric arc at the same radius as the source. In most cases, CT detector assemblies may include a collimator that collimates the detector elements to the source. In effect, each axial detector row may be collimated to a fan beam.

In some embodiments, the first radiation source 114 and the imaging assembly may be mounted on the same rotary ring. In some embodiments, the first radiation source 114 and the imaging assembly may simultaneously rotate around the subject. In this configuration, radiation treatment may be delivered simultaneously or alternately with imaging by moving the subject by only a small distance or without the need to move the subject between different treatment and imaging positions. Issues stemming from different amounts of treatment couch sag at such different treatment and imaging positions may be reduced or eliminated. Moreover, such imaging may detect gross subject motion (e.g., the motion of the body of the subject during the treatment and/or imaging) and/or motion associated with physiological processes (e.g., respiratory motion, cardiac motion, muscle contraction and relaxation). Owing to gross motion and/or physiological motion, the target volume within the subject to move so that the radiation beam may miss the target volume and may instead be delivered to a healthy tissue.

In some embodiments, the rotary ring may rotate at a relatively fast speed so that the imaging assembly may acquire relatively high-quality images associated with the target volume from two or more view positions. To allow simultaneous or alternating imaging and treatment, the first radiation source 114 mounted on the same rotary ring may be configured to emit a plurality of radiation beams to deliver radiation to the subject when the first radiation source 114 rotates at a relatively high speed. In some embodiments, the therapeutic radiation delivery apparatus 110 may further include a multi-leaf collimator (MLC) (not shown in FIG. 1). The MLC may be configured to define a plurality of segment shapes (also referred to as beam shapes). The MLC may include multiple leaves. More descriptions regarding the therapeutic radiation delivery apparatus 110 may be found in, for example, PCT Application No. PCT/CN2018/085266 entitled "RADIATION SYSTEMS FOR RADIATION TREATMENT AND IMAGING" filed on even date, the contents of which are hereby incorporated by reference.

The network 120 may facilitate exchange of information and/or data. In some embodiments, one or more components of the radiation system 100 (e.g., the therapeutic radiation delivery apparatus 110, the terminal 130, the processing device 140, or the storage device 150) may send information and/or data to another component(s) in the radiation system 100 via the network 120. For example, the processing device 140 may cause, via the network 120, the first radiation source 114 of the therapeutic radiation delivery apparatus 110 to emit radiation beams. As another example, the processing device 140 may obtain, via the network 120, user instruction(s) for generating images, adjusting a treatment plan, delivering radiation according to a treatment plan, etc. In some embodiments, the network 120 may be any type of wired or wireless network, or combination thereof. The network 120 may be and/or include a public network (e.g., the Internet), a private network (e.g., a local area network (LAN), a wide area network (WAN)), etc.), a wired network (e.g., an Ethernet network), a wireless network (e.g., an 802.11 network), a Wi-Fi network), a cellular network (e.g., a Long Term Evolution (LTE) network), a frame relay network, a virtual private network ("VPN"), a satellite network, a telephone network, routers, hubs, switches, server computers, and/or any combination thereof. Merely by way of example, the network 120 may include a cable network, a wireline network, an optical fiber network, a telecommunications network, an intranet, an Internet, a local area network (LAN), a wide area network (WAN), a wireless local area network (WLAN), a metropolitan area network (MAN), a wide area network (WAN), a public telephone switched network (PSTN), a Bluetooth™ network, a ZigBee™ network, a near field communication (NFC) network, or the like, or any combination thereof. In some embodiments, the network 120 may include one or more network access points. For example, the network 120 may include wired or wireless network access points such as base stations and/or internet exchange points through which one or more components of the radiation system 100 may be connected to the network 120 to exchange data and/or information.

The terminal 130 include a mobile device 130-1, a tablet computer 130-2, a laptop computer 130-3, or the like, or any combination thereof. In some embodiments, the mobile device 130-1 may include a smart home device, a wearable device, a smart mobile device, a virtual reality device, an augmented reality device, or the like, or any combination thereof. In some embodiments, the smart home device may include a smart lighting device, a control device of an intelligent electrical apparatus, a smart monitoring device, a smart television, a smart video camera, an interphone, or the like, or any combination thereof. In some embodiments, the wearable device may include a bracelet, footgear, eyeglasses, a helmet, a watch, clothing, a backpack, an accessory, or the like, or any combination thereof. In some embodiments, the smart mobile device may include a smartphone, a personal digital assistant (PDA), a gaming device, a navigation device, a point of sale (POS) device, or the like, or any combination thereof. In some embodiments, the virtual reality device and/or the augmented reality device may include a virtual reality helmet, a virtual reality glass, a virtual reality patch, an augmented reality helmet, an augmented reality glass, an augmented reality patch, or the like, or any combination thereof. For example, the virtual reality device and/or the augmented reality device may include a Google Glass, an Oculus Rift, a HoloLens, a Gear VR, etc. In some embodiments, the terminal 130 may remotely operate the therapeutic radiation delivery apparatus 110. In some embodiments, the terminal 130 may operate the therapeutic radiation delivery apparatus 110 via a wireless connection. In some embodiments, the terminal 130 may receive information and/or instructions inputted by a user, and send the received information and/or instructions to the therapeutic radiation delivery apparatus 110 or to the processing device 140 via the network 120. In some embodiments, the terminal 130 may receive data and/or information from the processing device 140. In some embodiments, the terminal 130 may be part of the processing device 140. In some embodiments, the terminal 130 may be omitted.

In some embodiments, the processing device 140 may process data obtained from the therapeutic radiation delivery apparatus 110, the terminal 130, or the storage device 150. For example, the processing device 140 may determine a radiation treatment plan based on a set of one or more optimization goals and/or one or more constraints (e.g., constraints of the therapeutic radiation delivery apparatus 110). In some embodiments, the processing device 140 may further cause the therapeutic radiation delivery apparatus 110 to deliver radiation to a subject based on the radiation treatment plan. The processing device 140 may be a central processing unit (CPU), a digital signal processor (DSP), a system on a chip (SoC), a microcontroller unit (MCU), or the like, or any combination thereof. In some embodiments, the processing device 140 may be a single server or a server group. The server group may be centralized or distributed. In some embodiments, the processing device 140 may be local or remote. For example, the processing device 140 may access information and/or data stored in the therapeutic radiation delivery apparatus 110, the terminal 130, and/or the storage device 150 via the network 120. As another example, the processing device 140 may be directly connected to the therapeutic radiation delivery apparatus 110, the terminal 130, and/or the storage device 150, to access stored information and/or data. In some embodiments, the processing device 140 may be implemented on a cloud platform. Merely by way of example, the cloud platform may include a private cloud, a public cloud, a hybrid cloud, a community cloud, a distributed cloud, an inter-cloud, a multi-cloud, or the like, or any combination thereof. In some embodiments, the processing device 140 may be implemented on a computing device 200 having one or more components illustrated in FIG. 2 in the present disclosure.

The storage device 150 may store data and/or instructions. In some embodiments, the storage device 150 may store data obtained from the terminal 130 and/or the processing device 140. In some embodiments, the storage device 150 may store data and/or instructions that the processing device 140 may execute or use to perform exemplary methods described in the present disclosure. In some embodiments, the storage device 150 may include a mass storage, removable storage, a volatile read-and-write memory, a read-only memory (ROM), or the like, or any combination thereof. Exemplary mass storage may include a magnetic disk, an optical disk, a solid-state drive, etc. Exemplary removable storage may include a flash drive, a floppy disk, an optical disk, a memory card, a zip disk, a magnetic tape, etc. Exemplary volatile read-and-write memory may include a random-access memory (RAM). Exemplary RAM may include a dynamic RAM (DRAM), a double date rate synchronous dynamic RAM (DDR SDRAM), a static RAM (SRAM), a thyristor RAM (T-RAM), and a zero-capacitor RAM (Z-RAM), etc. Exemplary ROM may include a mask ROM (MROM), a programmable ROM (PROM), an erasable programmable ROM (PEROM), an electrically erasable programmable ROM (EEPROM), a compact disk ROM (CD-ROM), and a digital versatile disk ROM, etc. In some embodiments, the storage device 150 may be implemented on a cloud platform. Merely by way of example, the cloud platform may include a private cloud, a public cloud, a hybrid cloud, a community cloud, a distributed cloud, an inter-cloud, a multi-cloud, or the like, or any combination thereof.

In some embodiments, the storage device 150 may be connected to the network 120 to communicate with one or more components of the radiation system 100 (e.g., the terminal 130, the processing device 140). One or more components of the radiation system 100 may access the data or instructions stored in the storage device 150 via the network 120. In some embodiments, the storage device 150 may be directly connected to or communicate with one or more components of the radiation system 100 (e.g., the terminal 130, the processing device 140). In some embodiments, the storage device 150 may be part of the processing device 140.

FIG. 2 is a schematic diagram illustrating exemplary hardware and/or software components of a computing device 200 on which the processing device 140 may be implemented according to some embodiments of the present disclosure. As illustrated in FIG. 2, the computing device 200 may include a processor 210, a storage 220, an input/output (I/O) 230, and a communication port 240.

The processor 210 may execute computer instructions (program code) and, when executing the instructions, cause the processing device 140 to perform functions of the processing device 140 in accordance with techniques described herein. The computer instructions may include, for example, routines, programs, objects, components, signals, data structures, procedures, modules, and functions, which perform particular functions described herein. In some embodiments, the processor 210 may process data and/or images obtained from the therapeutic radiation delivery apparatus 110, the terminal 130, the storage device 150, and/or any other component of the radiation system 100. For example, the processor 210 may generate a radiation treatment plan. As another example, the processor 210 may adjust a radiation treatment plan based on, e.g., one or more imaging protocols. As a further example, the processor 210 may cause the therapeutic radiation delivery apparatus 110 to deliver radiation to a subject according to the generated radiation treatment plan. In some embodiments, the processor 210 may include one or more hardware processors, such as a microcontroller, a microprocessor, a reduced instruction set computer (RISC), an application specific integrated circuits (ASICs), an application-specific instruction-set processor (ASIP), a central processing unit (CPU), a graphics processing unit (GPU), a physics processing unit (PPU), a microcontroller unit, a digital signal processor (DSP), a field programmable gate array (FPGA), an advanced RISC machine (ARM), a programmable logic device (PLD), any circuit or processor capable of executing one or more functions, or the like, or any combinations thereof.

Merely for illustration, only one processor is described in the computing device 200. However, it should be noted that the computing device 200 in the present disclosure may also include multiple processors. Thus operations and/or method steps that are performed by one processor as described in the present disclosure may also be jointly or separately performed by the multiple processors. For example, if in the present disclosure the processor of the computing device 200 executes both process A and process B, it should be understood that process A and process B may also be performed by two or more different processors jointly or separately in the computing device 200 (e.g., a first processor executes process A and a second processor executes process B, or the first and second processors jointly execute processes A and B).

The storage 220 may store data/information obtained from the therapeutic radiation delivery apparatus 110, the terminal 130, the storage device 150, or any other component of the radiation system 100. In some embodiments, the storage 220 may include a mass storage device, removable storage device, a volatile read-and-write memory, a read-only memory (ROM), or the like, or any combination thereof. For example, the mass storage may include a magnetic disk, an optical disk, a solid-state drive, etc. The removable storage may include a flash drive, a floppy disk, an optical disk, a memory card, a zip disk, a magnetic tape, etc. The volatile read-and-write memory may include a random access memory (RAM). The RAM may include a dynamic RAM (DRAM), a double date rate synchronous dynamic RAM (DDR SDRAM), a static RAM (SRAM), a thyristor RAM (T-RAM), and a zero-capacitor RAM (Z-RAM), etc. The ROM may include a mask ROM (MROM), a programmable ROM (PROM), an erasable programmable ROM (PEROM), an electrically erasable programmable ROM (EEPROM), a compact disk ROM (CD-ROM), and a digital versatile disk ROM, etc. In some embodiments, the storage 220 may store one or more programs and/or instructions to perform exemplary methods described in the present disclosure. For example, the storage 220 may store a program (e.g., in the form of computer-executable instructions) for the processing device 140 for generating a radiation treatment plan. As another example, the storage 220 may store a program (e.g., in the form of computer-executable instructions) for the processing device 140 for cause the therapeutic radiation delivery apparatus 110 to deliver radiation to a subject based on the radiation treatment plan.

The I/O 230 may input or output signals, data, and/or information. In some embodiments, the I/O 230 may enable a user interaction with the processing device 140. In some embodiments, the I/O 230 may include an input device and an output device. Exemplary input devices may include a keyboard, a mouse, a touch screen, a microphone, or the like, or a combination thereof. Exemplary output devices may include a display device, a loudspeaker, a printer, a projector, or the like, or a combination thereof. Exemplary display devices may include a liquid crystal display (LCD), a light-emitting diode (LED)-based display, a flat panel display, a curved screen, a television device, a cathode ray tube (CRT), or the like, or a combination thereof.

The communication port 240 may be connected to a network (e.g., the network 120) to facilitate data communications. The communication port 240 may establish connections between the processing device 140 and the therapeutic radiation delivery apparatus 110, the terminal 130, or the storage device 150. The connection may be a wired connection, a wireless connection, or combination of both that enables data transmission and reception. The wired connection may include an electrical cable, an optical cable, a telephone wire, or the like, or any combination thereof. The wireless connection may include Bluetooth, Wi-Fi, WiMAX, WLAN, ZigBee, mobile network (e.g., 3G, 4G, 5G, etc.), or the like, or a combination thereof. In some embodiments, the communication port 240 may be a standardized communication port, such as RS232, RS485, etc. In some embodiments, the communication port 240 may be a specially designed communication port. For example, the communication port 240 may be designed in accordance with the digital imaging and communications in medicine (DICOM) protocol.

Figure 3:
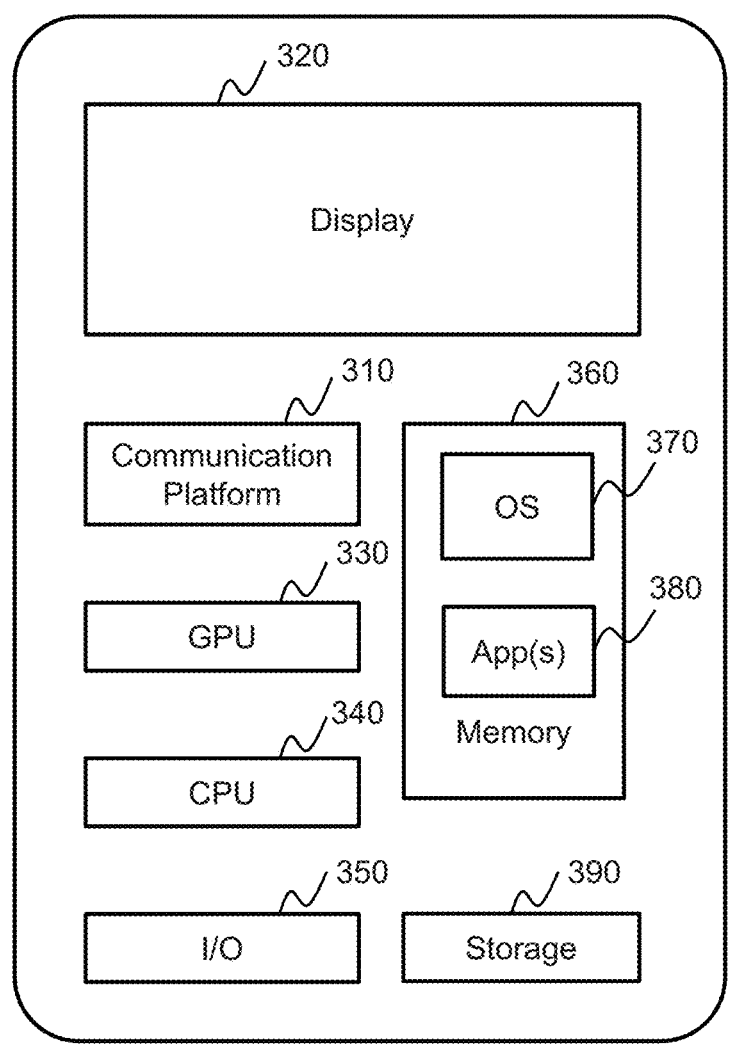
FIG. 3 is a schematic diagram illustrating exemplary hardware and/or software components of an exemplary mobile device according to some embodiments of the present disclosure.

FIG. 3 is a schematic diagram illustrating exemplary hardware and/or software components of a mobile device 300 according to some embodiments of the present disclosure. As illustrated in FIG. 3, the mobile device 300 may include a communication platform 310, a display 320, a graphic processing unit (GPU) 330, a central processing unit (CPU) 340, an VO 350, a memory 360, and a storage 390. In some embodiments, any other suitable component, including but not limited to a system bus or a controller (not shown), may also be included in the mobile device 300. In some embodiments, a mobile operating system 370 (e.g., iOS, Android, Windows Phone, etc.) and one or more applications 380 may be loaded into the memory 360 from the storage 390 in order to be executed by the CPU 340. The applications 380 may include a browser or any other suitable mobile apps for receiving and rendering information relating to image processing or other information from the processing device 140. User interactions with the information stream may be achieved via the I/O 350 and provided to the processing device 140 and/or other components of the radiation system 100 via the network 120.

To implement various modules, units, and their functionalities described in the present disclosure, computer hardware platforms may be used as the hardware platform(s) for one or more of the elements described herein. The hardware elements, operating systems and programming languages of such computers are conventional in nature, and it is presumed that those skilled in the art are adequately familiar therewith to adapt those technologies to generate a radiation treatment plan as described herein. A computer with user interface elements may be used to implement a personal computer (PC) or another type of work station or terminal device, although a computer may also act as a server if appropriately programmed. It is believed that those skilled in the art are familiar with the structure, programming and general operation of such computer equipment and as a result, the drawings should be self-explanatory.

Figure 4:
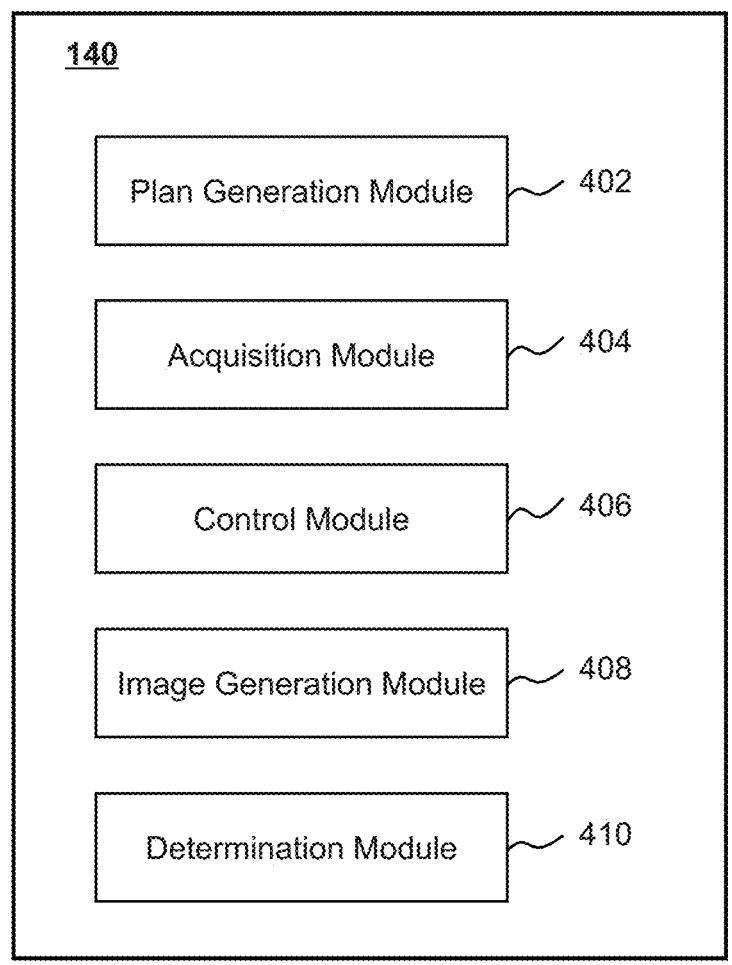
FIG. 4 is a block diagram illustrating an exemplary processing device according to some embodiments of the present disclosure.

FIG. 4 is a schematic diagram illustrating an exemplary processing device according to some embodiments of the present disclosure. The processing device 140 may be implemented on the computing device 200 (e.g., the processor 210 as illustrated in FIG. 2 or the CPU 340 as illustrated in FIG. 3). The processing device 140 may include a plan generation module 402, an acquisition module 404, a control module 406, an image generation module 408, and a determination module 410.

The plan generation module 402 may be configured to generate a plan for radiation delivery (also referred to herein as radiation treatment plan) from a radiation source (e.g., the first radiation source 114). The plan may be suitable for a radiation therapy delivered by a therapeutic radiation delivery apparatus including a treatment radiation source (e.g., the first radiation source 114) rotatable at a relatively high rotation speed. The plan may include a plurality of radiation segments. Each radiation segments may be characterized by at least one parameter selected from a start angle, a stop angle, a 2D segment shape, and/or a radiation dose (also referred to herein as a segment MU value). In some embodiments, the plan generation module 402 may optimize the plurality of radiation segments to meet a set of one or more optimization goals by superimposing at least two radiation segments from at least two different rotations into a target volume of a subject.

In some embodiments, the plan generation module 402 may determine the radiation treatment plan based on a set of one or more optimization goals that are set by a healthcare professional (e.g., a radiation oncologist, a radiation physicist, a radiation technician, etc.). Alternatively or additionally, the plan generation module 402 may determine the radiation treatment plan based on one or more constraints that are associated with the therapeutic radiation delivery apparatus 110. In some embodiments, during the determination of the radiation treatment plan, the plan generation module 402 may optimize the radiation treatment plan to meet the set of one or more optimization goals and/or the constraint(s). More descriptions of the determination and/or optimization of the radiation treatment plan may be found elsewhere in the present disclosure (e.g., FIGS. 6-10 and the descriptions thereof).

The acquisition module 404 may be configured to obtain information related to radiation system 100. In some embodiments, the acquisition module 404 may obtain one or more constraints of the therapeutic radiation delivery apparatus 110. The constraint(s) may be used to determine the radiation treatment plan. In some embodiments, the acquisition module 404 may obtain one or more imaging protocols that are to be executed during radiation therapy, an execution interval of the one or more imaging protocols, and/or an execution sequence of the one or more imaging protocols. The imaging protocol may include an acquisition protocol and/or a reconstruction protocol. In some embodiments, the acquisition module 404 may obtain a set of one or more optimization goals for radiation delivery by a therapeutic radiation delivery apparatus that are used to determine a radiation treatment plan. In some embodiments, the acquisition module 404 may obtain a radiation treatment plan related to a subject to perform a radiation therapy on the subject.

The control module 406 may be configured to control one or more operations of the therapeutic radiation delivery apparatus 110. In some embodiments, the control module 406 may cause a radiation source (e.g., the first radiation source 114) and an imaging assembly (e.g., the second radiation source 113, the detector module 112) to rotate around a subject. For example, the control module 406 may control the first radiation source 114 and the imaging assembly to rotate at a relatively high speed. In some embodiments, the control module 406 may cause the first radiation source 114 to deliver radiation to the subject when the radiation source is rotating, e.g., at a relatively high speed. Alternatively, the control module 406 may also cause the first radiation source 114 to stop and/or pause the radiation delivery to the subject.

The image generation module 408 may be configured to generate one or more images of the subject. In some embodiments, the image generation module 408 may generate one or more planned images of the subject that are used to generate the radiation treatment plan. Alternatively, the image generation module 408 may generate one or more images of the subject while the first radiation source 114 is delivering radiation to the subject.

The determination module 410 may be configured to determine whether a radiation treatment plan is suitable for a radiation therapy delivered by the first radiation source 114 rotatable at a relatively high rotation speed. In response to a determination that the radiation treatment plan is not suitable for a radiation therapy delivered by the first radiation source 114 rotatable at a relatively high rotation speed, the radiation treatment plan may be adjusted. Alternatively or additionally, the determination module 410 may determine whether there is a movement related to the subject based on the one or more images generated during the radiation therapy. In some embodiments, in response to a determination that the movement related to the subject exceeds a threshold, the delivery of the radiation to the subject may be stopped or paused.

It should be noted that the above description is merely provided for the purposes of illustration, and not intended to limit the scope of the present disclosure. For persons having ordinary skills in the art, multiple variations and modifications may be made under the teachings of the present disclosure. However, those variations and modifications do not depart from the scope of the present disclosure. For example, the processing device 140 may further include a storage module (not shown in FIG. 4). The storage module may be configured to store data generated by the processing device 140. As another example, some of the modules may be installed in a different device separated from the other modules. Merely by way of example, the plan generation module 402 may reside in a first device, and other modules may reside on a second device.

Figure 5:
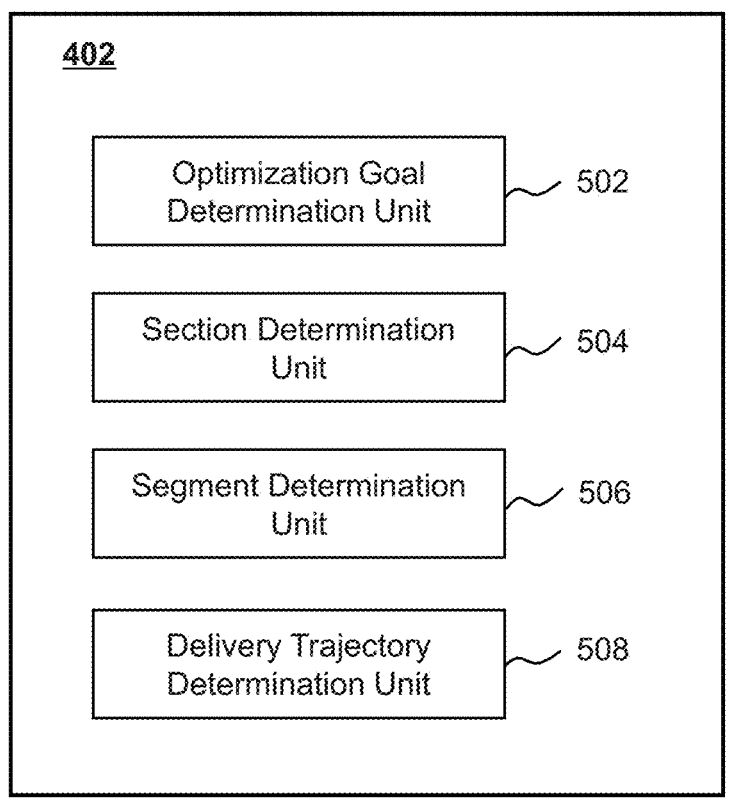
FIG. 5 is a block diagram illustrating an exemplary plan generation module according to some embodiments of the present disclosure.

FIG. 5 is a schematic diagram illustrating an exemplary plan generation module according to some embodiments of the present disclosure. The processing device 140 (e.g., the plan generation module 402) may be implemented on the computing device 200 (e.g., the processor 210 as illustrated in FIG. 2, the CPU 340 as illustrated in FIG. 3). The plan generation module 402 may include an optimization goal determination unit 502, a section determination unit 504, a segment determination unit 506, and a delivery trajectory determination unit 508.

The optimization goal determination unit 502 may be configured to determine a set of one or more optimization goals for radiation delivery by a therapeutic radiation delivery apparatus. In some embodiments, the set of one or more optimization goals may relate to one or more dose constraints, one or more target volumes (e.g., the geometry of the target volumes, the position of the target volumes), one or more structures outside of the target volume(s) (e.g., the geometry of the structures, the position of the structures), the delivery time, etc. In some embodiments, the target volume may include one or more tumors and/or one or more OARs.

In some embodiments, a longer delivery time may affect the accuracy of the dose delivery due to, for example, the movement of a subject. The optimization goal determination unit 502 may determine a suitable delivery time to reduce or eliminate effects caused by the subject. In some embodiments, the optimization goal determination unit 502 may determine a weight for one or more of the optimization goals (e.g. the prescribed dose associated with the target volume, the prescribed dose associated with the OAR, etc.). In some embodiments, the weight for one or more of the optimization goals may be set by a user. Merely by way of example, if the target volume is a tumor and an OAR (a structure outside of the target volume) is a vital organ (e.g., heart, lungs), the optimization goal determination unit 502 may give a relatively small weight to the prescribed dose associated with the target volume and a relatively large weight to the prescribed dose associated with the OAR. As another example, if the target volume is a malignant tumor and the OAR is not vital organ(s) (e.g., a blood vessel, muscle), the optimization goal determination unit 502 may give a relatively large weight to the prescribed dose associated with the target volume and a relatively small weight to the prescribed dose associated with the OAR.

In some embodiments, the dose constraint(s) may be prescribed by one or more healthcare professionals (e.g., a radiation oncologist, a radiation physicist, a radiation technician, etc.) according to one or more previously generated images related to the target volume. Alternatively, the optimization goal(s) may be adjusted or provided by the healthcare professional(s). In some embodiments, the optimization goal(s) may be stored in a storage device (e.g., the storage device 150), and the optimization goal determination unit 502 may obtain the optimization goal(s) from the storage device 150.

The section determination unit 504 may be configured to determine a plurality of sections of a rotational movement of a radiation source (e.g., the first radiation source 114) of the therapeutic radiation delivery apparatus (e.g., the therapeutic radiation delivery apparatus 110). In some embodiments, the rotational movement of the first radiation source 114 may correspond to a rotation range. In some embodiments, the rotation range of the rotational movement of the radiation source may be 0°-360° or a subset of 0°-360° (e.g., 0°-180°, 180°-360°, 100°-200°, etc.). In some embodiments, the rotation range of the rotational movement of the first radiation source 114 may be segmented into a plurality of sections for one or more times. A section may correspond to an angle range in which radiation may be delivered during radiation therapy. Each section may have an angle range. More descriptions of the plurality of sections may be found elsewhere in the present disclosure (e.g., operation 603 of the process 600 and the relevant descriptions thereof).

In some embodiments, the section determination unit 504 may segment the rotation range of the rotational movement randomly or uniformly to obtain the plurality of sections. Alternatively, the section determination unit may determine the plurality of sections based on the set of one or more optimization goals. For example, the section determination unit 504 may determine, by analyzing the optimization goal(s), a plurality of first angle ranges in which radiation needs to be delivered and a plurality of second angle ranges in which no radiation needs to be delivered (or radiation needs to be avoided), and further designate the first angle ranges as the sections. Alternatively, the section determination unit 504 may determine the plurality of sections based on the set of one or more optimization goals and/or one or more constraints associated with the therapeutic radiation delivery apparatus 110.

The segment determination unit 506 may be configured to determine a plurality of radiation segments by iteratively optimizing a dose distribution relative to the set of one or more optimization goals. In some embodiments, the segment determination unit 506 may determine one or more parameters including a number of the plurality of radiation segments (or referred to as the segment count), an angle range of each of the plurality of radiation segments, one or more segment shapes of each of the plurality of radiation segments, one or more segment MU values of each of the plurality of radiation segments, one or more segment MU rates of each of the plurality of radiation segments, or the like, or a combination thereof. More descriptions of the radiation segments may be found elsewhere in the present disclosure (e.g., operation 605 of the process 600 and the relevant descriptions thereof).

In some embodiments, the segment determination unit 506 may, by performing an iterative optimization, determine the plurality of radiation segments based on the plurality of sections. In the iterative optimization, desirable segment shapes, segment MU values, and/or radiation segments may be determined. In some embodiments, one or more iterations may be performed in iterative optimization until a dose distribution satisfies the optimization goals. In the first iteration, a plurality of radiation segments and the corresponding angle ranges, segment shapes and segment MU values may be determined. In the other iterations, the radiation segments and the corresponding angle ranges, segment shapes, and segment MU values may be updated, and accordingly, a dose distribution may be determined based on the updated radiation segments, and updated angle ranges, updated segment shapes, and updated segment MU values of the updated radiation segments, and then a characteristic value indicating how closely the dose distribution satisfies the optimization goals may be determined. In some embodiments, the iteration may be terminated until one or more conditions are satisfied. In some embodiments, the segment determination unit 506 may determine the plurality of radiation segments by iteratively optimizing the dose distribution relative to the set of one or more optimization goals based on one or more constraints associated with the therapeutic radiation delivery apparatus.

In some embodiments, the segment determination unit 506 may optimize the plurality of radiation segments by direct optimization of segment shapes, start angles, stop angles, and segment MU values of the plurality of radiation segments, which is also referred to as a DAO process. In the DAO process, a plurality of initial segments may be determined. Each of the plurality of initial segments may include an initial segment shape, an initial angle range (including an initial start angle and an initial stop angle), an initial segment MU rate, and/or an initial segment MU value. In some embodiments, the initial segments may be set according to a default setting of the radiation system 100 or preset by a user or operator via the terminals 130. The initial segments and/or the segment count of the plurality of radiation segments may be updated during the iterative optimization until optimization criteria associated with the set of one or more optimization goals are met.

Alternatively, the segment determination unit 506 may optimize the plurality of radiation segments according to an FMO process. In the FMO process, the segment determination unit 506 may generate a fluence map by iteratively optimizing the dose distribution relative to the set of one or more optimization goals. The fluence map may include a plurality of elements. Each element of the fluence map may represent an MU value of a sub-field segment. The segment determination unit 506 may determine the plurality of radiation segments based on the determined fluence map. In some embodiments, the segment determination unit 506 may adjust the sub-field segments to determine the plurality of radiation segments based on the fluence map.

In some embodiments, the segment determination unit 506 may optimize the segment count of the plurality of radiation segments to meet the set of one or more optimization goals. For example, the segment determination unit 506 may determine the segment count of the plurality of radiation segments by performing a plurality of iterations. During the plurality of iterations, an estimated segment count may successively increase from a relatively small value until one or more optimization criteria associated with the set of one or more optimization goals are met.

In some embodiments, the segment determination unit 506 may determine, in at least one iteration, a plurality of sub-segments of at least one radiation segment of the plurality of radiation segments based on one or more control points. In some embodiments, a radiation segment may include one or more control points, which may define the starting points and/or ending points of the sub-segments. In some embodiments, the segment determination unit 506 may determine a collimator angle of the MLC of the therapeutic radiation delivery apparatus 110 and a segment shape for each control point of the one or more control points, and further determine a segment MU value for each sub-segment of the plurality of sub-segments. The segment shapes and the segment MU values of two sub-segments may be different. In some embodiments, the segment determination unit 506 may further iteratively optimize the dose distribution relative to the set of one or more optimization goals based on the plurality of sub-segments and the plurality of radiation segments excluding the at least one radiation segment that has the plurality of sub-segments.

The intensity (also referred to as MU rate) of the radiation source (e.g., the first radiation source 114) may be changed in various ways. In some embodiments, a linear accelerator of the radiation source may be operated in a pulsed mode, under which radiation may be produced in short pulses (each pulse may last, for example, 3 microseconds), while the intensity may remain constant during each pulse. For example, in order to achieve a change of (average) intensity, the duration of a pulse or the frequency of a plurality of pulses may be adjusted such that over a period of time (for example, 100 microseconds to 1 second), the averaged intensity of the radiation beam is changed. In some embodiments, this averaged intensity may be referred to as the "dose rate" or "output rate" of the linear accelerator and is typically expressed in Monitor Units (MU) per minute (also referred to as MU rate). An MU is a measure of machine radiation output. It may be calibrated to a dose absorbed in a standardized phantom at a standardized position, under standardized conditions of irradiation. An MU rate may refer to the number of MU that are produced per unit time. In the present disclosure, the terms "MU rate" and "dose rate" are used interchangeably. However, in the strict sense a dose rate may depend not only on the machine radiation output, but also the properties of the subject to which radiation is imparted. In radiation therapy, the dose to be absorbed by a target volume (e.g., diseased tissue) may be prescribed. A planning and/or delivery system (e.g., the radiation system 100) may determine a sequence of parameters (such as MU value, MU rate) associated with the radiation source to achieve this level of absorbed dose in a target volume of the subject.

Thus, in an exemplary treatment plan, one of the parameters associated with the radiation source that is optimized may be the dose to be absorbed by the target volume. The parameter dose may be linearly proportional to the parameter MU, as long as the exposed subject and irradiation conditions do not change. As such, the dose rate may express the speed with which a certain dose is delivered. If all other parameters (including, but not limited to, beam shape or source position) remain constant, the impact of a change in the dose rate itself may be limited, since the spatial distribution of the dose in the target volume is not affected by different dose rates. If, however, during the delivery, any other parameter such as the beam shape of the position of the radiation source is modified or changed, a change in dose rate may affect how the dose is distributed over the target volume. Under such conditions, the dose rate itself may also need to be optimized in order to achieve the desired dose distribution.

The delivery trajectory determination unit 508 may be configured to determine a sequence of the plurality of radiation segments for radiation delivery to obtain a delivery trajectory of the radiation source of the therapeutic radiation delivery apparatus. In some embodiments, the processing device 140 may determine the radiation treatment plan based on the plurality of sequential radiation segments for radiation delivery and the delivery trajectory of the radiation source of the therapeutic radiation delivery apparatus. In some embodiments, the delivery trajectory may include a plurality of radiation segments, and each radiation segment may have one or more segment shapes, and one or more segment MU values. In some embodiments, a radiation segment may include a plurality of sub-segments, each sub-segment may have an angle range, one or more segment shapes and a segment MU value. In some embodiments, the delivery trajectory determination unit 508 may determine the delivery trajectory of the radiation source (e.g., the first radiation source 114) based on the plurality of radiation segments and one or more constraints associated with the therapeutic radiation delivery apparatus 110.

In some embodiments, the delivery trajectory may include multiple rotations. In some embodiments, a rotation of the delivery trajectory may correspond to a rotation of the radiation source. In some embodiments, the plurality of radiation segments may be distributed in the multiple rotations. In some embodiments, the segment MU value of a radiation segment may be delivered or distributed in one or more rotations. In some embodiments, a rotation may include one or more radiation segments. More descriptions of the rotations of the delivery trajectory may be found elsewhere in the present disclosure (e.g., operation 607 of the process 600 and the relevant descriptions thereof).

In some embodiments, the plurality of radiation segments may be arranged over at least two different rotations, and at least two radiation segments of the plurality of radiation segments may be at least partially overlapping with each other. Alternatively, the plurality of radiation segments may be arranged over at least two rotations of the first radiation source 114 in an interleaving pattern. More descriptions regarding the radiation segments may be found elsewhere in the present disclosure (e.g., operation 1103 of the process 1100 and the relevant descriptions thereof).

It should be noted that the above description is merely provided for the purposes of illustration, and not intended to limit the scope of the present disclosure. For persons having ordinary skills in the art, multiple variations and modifications may be made under the teachings of the present disclosure. However, those variations and modifications do not depart from the scope of the present disclosure. In some embodiments, two or more of the modules (or units) may be combined into a single module (or unit), and any one of the modules may be divided into two or more units (or sub-units). For example, the segment determination unit 506 and the delivery trajectory determination unit 508 may be integrated into a single unit configured to perform the functions thereof. As another example, the segment determination unit 506 may be divided into two sub-units. The first sub-unit may be configured to determine a plurality of radiation segments. The second sub-unit may be configured to determine a plurality of sub-segments of at least one radiation segment of the plurality of radiation segments.

In some embodiments, it may be desirable to ensure that a target volume (e.g., a tumor) of a subject receives sufficient radiation and that damage to the healthy tissue surrounding the target volume is minimized during the radiation delivery. It may be convenient for image-guided radiation therapy (IGRT) if a first radiation source and a second radiation source (e.g., a radiation source for delivering treatment radiation in a radiation therapy [or referred to as a treatment radiation source for brevity] and an X-ray tube of an imaging assembly for delivering imaging radiation [or referred to as an imaging radiation source for brevity]) are mounted on a rotary ring. In some situations, the treatment radiation source may rotate at a relatively high speed along with the imaging radiation source to generate relatively high-quality images associated with a target volume. Thus, it is desirable to generate a radiation treatment plan of a radiation therapy delivered by a therapeutic radiation delivery apparatus including a treatment radiation source rotatable at a relatively high rotation speed. In some embodiments, the radiation treatment plan may be determined based on a set of one or more optimization goals that are set by a healthcare professional (e.g., a radiation oncologist, a radiation physicist, a radiation technician, etc.). In some embodiments, the radiation treatment plan may be determined based on one or more constraints that are associated with the therapeutic radiation delivery apparatus 110. In some embodiments, during the determination of the radiation treatment plan, the radiation treatment plan may be optimized to meet the set of one or more optimization goals and/or the constraint(s). More descriptions of the determination and/or optimization of the radiation treatment plan may be found elsewhere in the present disclosure (e.g., FIGS. 6-10 and the descriptions thereof).

Figure 6:
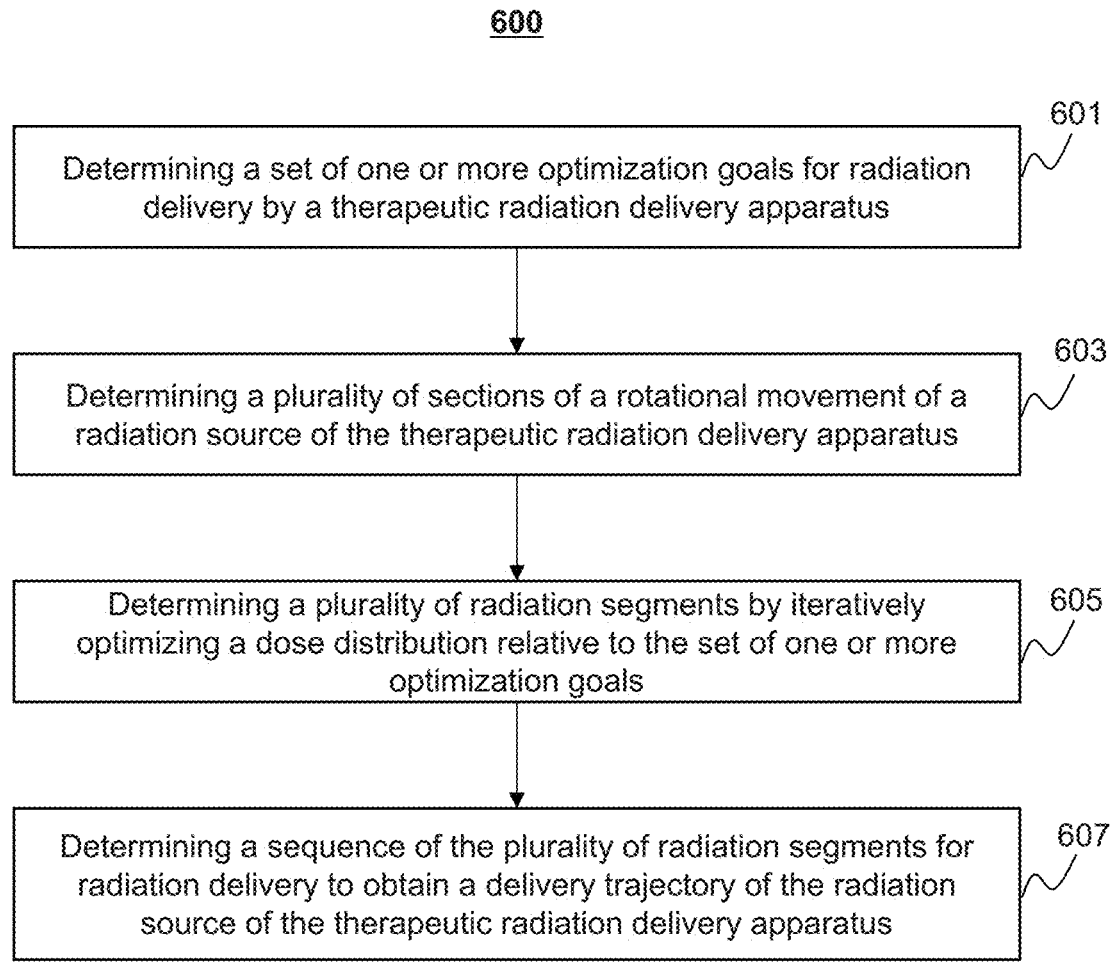
FIG. 6 is a flowchart illustrating an exemplary process for determining a radiation treatment plan according to some embodiments of the present disclosure.

FIG. 6 is a flowchart illustrating an exemplary process for determining a radiation treatment plan according to some embodiments of the present disclosure. In some embodiments, one or more operations of process 600 illustrated in FIG. 6 may be performed by the processing device 140 (e.g., the plan generation module 402). In some embodiments, one or more operations of process 600 may be implemented in the radiation system 100 illustrated in FIG. 1. For example, the process 600 may be stored in the storage device 150 and/or the storage 220 in the form of instructions (e.g., an application), and invoked and/or executed by the processing device 140 (e.g., the processor 210 of the computing device 200 as illustrated in FIG. 2, the CPU 340 of the mobile device 300 as illustrated in FIG. 3, one or more modules of the processing device 140 as illustrated in FIG. 4, one or more units of the plan generation module 402 as illustrated in FIG. 5, or the like). As another example, a portion of the process 600 may be implemented on the therapeutic radiation delivery apparatus 110. The operations of the illustrated process presented below are intended to be illustrative. In some embodiments, the process 600 may be accomplished with one or more additional operations not described, and/or without one or more of the operations discussed. Additionally, the order in which the operations of the process 600 as illustrated in FIG. 6 and described below is not intended to be limiting.

In 601, the processing device 140 (e.g., the optimization goal determination unit 502) may determine a set of one or more optimization goals for radiation delivery by a therapeutic radiation delivery apparatus (e.g., the therapeutic radiation delivery apparatus 110). In some embodiments, the set of one or more optimization goals may relate to one or more dose constraints, one or more target volumes (e.g., the geometry of the target volumes, the position of the target volumes), one or more structures outside of the target volume(s) (e.g., the geometry of the structures, the position of the structures), the delivery time, etc. Merely by way of example, the set of one or more optimization goals may include a desired dose distribution in a target volume (e.g., a tumor), a desired uniformity of the dose distribution in the target volume, a desired minimum dose delivered to the target volume, a desired maximum dose delivered to the target volume, a maximum dose that can be accepted by a structure outside of the target volume (e.g., an organ at risk [OAR]), a maximum time needed for radiation delivery, or the like, or any combination thereof. The OAR in the present disclosure may refer to a cell, an organ or tissue that is located in the vicinity of the target volume and under the risk of radiation damage due to the exposure to radiation delivered toward the target volume. In some embodiments, the dose constraint(s) may be measured by a dose volume histogram (DVH), which may reflect a relationship between dose and volume. For example, 95% of the target volume(s) may receive a prescribed dose associated with the target volume(s), and 2% of the OAR(s) may receive radiation that exceeds a prescribed dose associated with the OAR(s).

In some embodiments, the optimization goal(s) may define delivery time. As longer delivery time may affect the accuracy of the dose delivery due to, for example, the movement of a subject, the optimization goal determination unit 502 may determine a suitable delivery time.

In some embodiments, the dose constraint(s) may be prescribed by one or more healthcare professionals (e.g., a radiation oncologist, a radiation physicist, a radiation technician, etc.) according to one or more previously generated images related to the target volume. In some embodiments, the optimization goal(s) may be adjusted or provided by the healthcare professional(s). For example, a radiation physicist may set one or more parameters relating to the dose constraint(s) based on one or more empirical values. As another example, the radiation physicist may adjust the parameter(s) (e.g., one or more weights relating to the dose constraint(s)). In some embodiments, the optimization goal(s) may be stored in the storage device 150, and the optimization goal determination unit 502 may obtain the optimization goal(s) from the storage device 150.

In some embodiments, the optimization goal determination unit 502 may determine a weight for one or more of the optimization goals (e.g., the prescribed dose associated with the target volume, the prescribed dose associated with the OAR, etc.). For example, if the target volume is a benign tumor and the OAR is a vital organ (e.g., heart, lungs), the optimization goal determination unit 502 may give a relatively small weight to the prescribed dose associated with the target volume and a relatively large weight to the prescribed dose associated with the OAR. As another example, if the target volume is a malignant tumor and the OAR is not vital organ(s) (e.g., a blood vessel, muscle), the optimization goal determination unit 502 may give a relatively large weight to the prescribed dose associated with the target volume and a relatively small weight to the prescribed dose associated with the OAR.

In 603, the processing device 140 (e.g., the section determination unit 504) may determine a plurality of sections of a rotational movement of a radiation source (e.g., the first radiation source 114) of the therapeutic radiation delivery apparatus (e.g., the therapeutic radiation delivery apparatus 110).

As described elsewhere in the present disclosure, the first radiation source 114 may be mounted on a rotary ring, and may rotate around a subject. In some embodiments, the first radiation source 114 may deliver radiation (or emit radiation beams) toward the subject during rotational movement. In some embodiments, an imaging assembly (e.g., the second radiation source 113, the detector module 112) of the therapeutic radiation delivery apparatus 100 and the first radiation source 114 may be mounted on the same rotary ring, and be rotated around the subject synchronously. In some embodiments, the imaging assembly may generate one or more images of a subject (e.g., the target volume) to monitor a position of the target volume, so that the radiation therapy may be guided based on the position of the target volume. Therefore, the radiation therapy may be performed simultaneously with the imaging operation during the rotation of the first radiation source 114 and the imaging assembly. In some embodiments, the respiratory movement (or the cardiac movement) of the subject may induce a position change of the target volume, and accordingly the first radiation source 114 and the imaging assembly may be rotated at a relatively high speed to ensure that images generated by the imaging assembly have relatively high quality (e.g., relatively high angular sampling rate, relatively large angular range of data used to produce each tomographic or tomosynthetic image, relatively high clarity, relatively low level of artifact, etc.). In some embodiments, the time of one revolution of the first radiation source 114 and the imaging assembly may be less than a half of the time of a respiratory cycle (or a half of the time of a cardiac cycle, or a half of the cycle of muscle contraction and relaxation, etc.) of the subject. In some embodiments, the time for one revolution of the first radiation source 114 and the imaging assembly may be several seconds or minutes (e.g., 1 second, 2 seconds, 3 seconds, 4 seconds, 5 seconds, 10 seconds, 30 seconds, 1 minute, 5 minutes, etc.). That is, the rotation speed of the rotational movement may be at a relatively high speed (e.g., 1 revolution/second).

A radiation dose delivered to a target volume (or a portion of the target volume) may be determined based on a rotation speed and an MU rate of the first radiation source 114. As the rotation speed of the first radiation source 114 may be relatively fast, the MU rate may need to be at a relatively high level to ensure that the target volume receives sufficient radiation (e.g., the MU rate may reach 10000 monitor unit (MU)/minute, 20000 MU/minute, 50000 MU/minute) in a relatively short time. However, the MU rate of the first radiation source 114 may not be increased infinitely due to physical limitations or constraints of the therapeutic radiation delivery apparatus (e.g., the maximal MU rate may be 2000 MU/minute, 5000 MU/minute, etc.). Therefore, the first radiation source 114 may rotate a plurality of rotations (or referred to as revolutions) to satisfy the desired radiation dose delivered to the target volume, and in one or more circles of the plurality of circles, a portion of the desired radiation dose may be delivered by the first radiation source 114. In some embodiments, the radiation dose corresponding to different angle ranges of a circle may be different. For example, a first radiation dose may be delivered for the angle range of 0°-20°, no radiation dose may be delivered for the angle range of 20°-50°, and a second radiation dose may be delivered for the angle range of 50°-60°. Alternatively, or additionally, the radiation dose corresponding to a same angle range of different circles may be different. For example, for a first circle, a first radiation dose corresponding to the angle range of 0°-20° may be delivered, while for a second circle, a second radiation dose corresponding to the angle range of 0°-20° may be delivered. Thus, a plurality of radiation segments having a plurality of radiation doses may need to be determined before the radiation therapy to precisely deliver radiation to the target volume and spare healthy tissue (including healthy tissue in the vicinity of the target volume) from radiation damage.

In some embodiments, the rotational movement of the first radiation source 114 may correspond to a rotation range. In some embodiments, the rotation range of the rotational movement of the radiation source may be 0°-360°. In some embodiments, the rotation range of the rotational movement of the radiation source may be a subset of 0°-360° (e.g., 0°-180°, 180°-360°, 100°-200°, etc.). In some embodiments, the rotation range of the rotational movement of the first radiation source 114 may be segmented into a plurality of sections for one or more times. A section may correspond to an angle range in which radiation may be delivered during radiation therapy. Each section may have an angle range. In some embodiments, the plurality of sections may correspond to a plurality of angle ranges. In some embodiments, the span of two of the sections may be different. Alternatively, the span of two of the sections may be the same. For example, the span of a first section may be 10° (e.g., an angle range of 30°-40°), while the span of a second section may be 15° (e.g., an angle range of 100°-115°). As another example, the span of the first section may be 20° (e.g., an angle range of 50°-70°), and the span of a third section may be 20° (e.g., an angle range of 90°-110°). In some embodiments, a first section may be adjacent to a second section. For example, the angle range of the first section may be 0°-20°, while the angle range of the second section may be 20°-50°. In some embodiments, the angle range of a first section may at least partially overlap with the angle range of a second section.

Figure 7A:
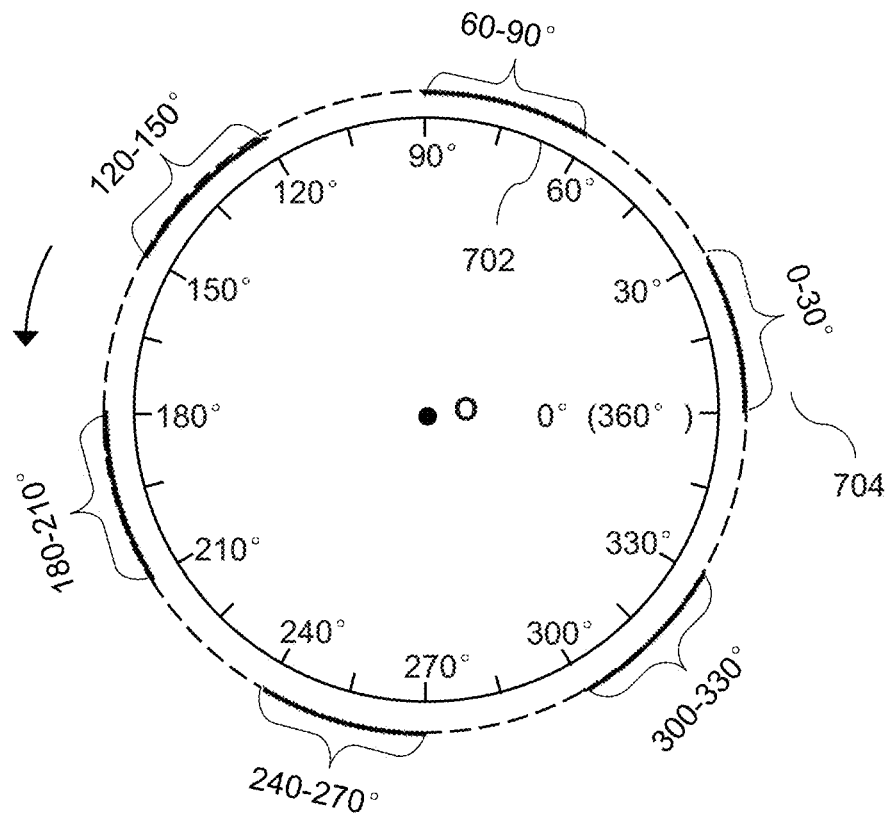
FIGS. 7A and 7B are schematic diagrams illustrating exemplary sections according to some embodiments of the present disclosure.
Figure 7B:
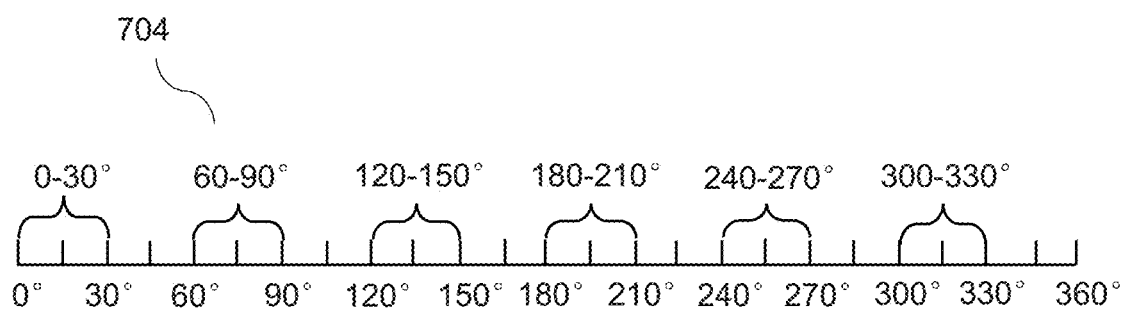

For example, the angle range of the first section may be 30°-50°, while the angle range of the second section may be 40°-70°. In some embodiments, the angle range of a first section may include the angle range of a second section. For example, the angle range of the first section may be 50°-100°, while the angle range of the second section may be 60°-90°. In some embodiments, there may be a blank range between a first section and a second section. The blank range may refer to a range in which no radiation is delivered during radiation therapy. For example, the angle range of the first section may be 200°-240°, while the angle range of the second section may be 300°-320°, and accordingly, the angle range of 240°-300° may indicate a blank range. As another example, as shown in FIGS. 7A and 7B, the angle range of a first section may be 60°-90°, while the angle range of a second section may be 120°-150°, and accordingly, the angle range of 90°-120° may indicate a blank range. In some embodiments, angle range(s) of one or more of the sections may span two consecutive circles. For example, the angle range of a section may be 350° of a first circle to 10° of a second circle immediately following the first circle. In some embodiments, the plurality of sections may have one or more relations illustrated above.

In some embodiments, the processing device 140 (e.g., the section determination unit 504) may determine the plurality of sections based on the set of one or more optimization goals. Merely by way of example, the section determination unit 504 may determine, by analyzing the optimization goal(s), a plurality of first angle ranges in which radiation needs to be delivered and a plurality of second angle ranges in which no radiation needs to be delivered (or radiation needs to be avoided), and further designate the first angle ranges as the sections. Alternatively, or additionally, the section determination unit 504 may determine the plurality of sections based on one or more constraints associated with the therapeutic radiation delivery apparatus. The constraints associated with the therapeutic radiation delivery apparatus may include one or more physical limitations of the therapeutic radiation delivery apparatus, for example, a maximal MU rate of the radiation source, a maximal rotation speed of the radiation source, a minimal rotation speed of the radiation source, an acceleration time of the radiation source, a deceleration time of the radiation source, a maximal acceleration of the radiation source, a maximal jerk of the radiation source, a deceleration velocity of the radiation source, a maximal leaf speed of a multi-leaf collimator (MLC) of the therapeutic radiation delivery apparatus, a motion range of multiple leaves of the MLC, a maximal leaf acceleration of the MLC, a maximal leaf jerk of the MLC, or the like, or any combination thereof. In some embodiments, the MU rate of the radiation source may be within a range of 0-5000 MU/min. In some embodiments, the MU rate of the radiation source may be within a range of 100-5000 MU/min. In some embodiments, the MU rate of the radiation source may be within a range of 1400-1800 MU/min.

In some embodiments, the processing device 140 (e.g., the section determination unit 504) may determine the plurality of sections that are randomly distributed or uniformly distributed. Merely by way of example, a plurality of uniform sections may be determined, such as the sections illustrated in FIGS. 7A and 7B. FIGS. 7A and 7B are schematic diagrams illustrating exemplary sections according to some embodiments of the present disclosure. As illustrated in FIG. 7A, the rotary ring 702 may rotate around the rotation center O clockwise or counterclockwise. One or more sections 704 are uniformly distributed on the rotary ring 702. The exemplary sections 704 may correspond to angle ranges 0°-30°, 60°-90°, 120°-150°, 180°-210°, 240°-270°, and 300°-330°. Merely for illustration purposes, the section(s) 704 may be expressed on a straight line section that represents the rotation range of 0°-360°, as shown in FIG. 7B. It should be noted that the descriptions of the section(s) 704 is merely for the purposes of illustration, and not intended to limit the scope of the present disclosure.

In some embodiments, a user (e.g., a healthcare professional) may specify information relating to the plurality of sections. In some embodiments, the information may be derived automatically by, e.g., the processing device 140 based on, e.g., empirical data, instructions provided by a user (e.g., a healthcare professional). The information may include one or more of the plurality of sections, the number of the plurality of sections (or referred to as the section count), span(s) of the angle ranges of the plurality of sections, or the like, or any combination thereof. In some embodiments, the healthcare professional may input the information via a user interface of the radiation system 100 (e.g., the I/O 230 of the computing device 200 illustrated in FIG. 2, the I/O 350 of the mobile device 300 illustrated in FIG. 3, etc.), and then the processing device 140 (e.g., the section determination unit 504) may determine the plurality of sections based on the information, the optimization goal(s), the constraint(s), or the like, or any combination thereof. In some embodiments, the information may be stored in a storage (e.g., the storage device 150, the storage 220, the storage 390, etc.), and then the section determination unit 504 may obtain the information via the acquisition module 404 and determine the sections.

In 605, the processing device 140 (e.g., the segment determination unit 506) may determine a plurality of radiation segments by iteratively optimizing a dose distribution relative to the set of one or more optimization goals. In some embodiments, the segment determination unit 506 may determine the plurality of radiation segments based on the plurality of sections determined in 603. In some embodiments, the segment determination unit 506 may determine one or more parameters including a number of the plurality of radiation segments (or referred to as the segment count), an angle range of each of the plurality of radiation segments, one or more segment shapes of each of the plurality of radiation segments, one or more segment MU values of each of the plurality of radiation segments, one or more segment MU rates of each of the plurality of radiation segments, or the like, or a combination thereof.

In some embodiments, when delivering the radiation, the first radiation source 114 may rotate to provide radiation beams from different positions or angles. The point at which the radiation beams converge or intersect may be generally referred to as a radiation isocenter. As a largest radiation dose of a radiation beam may be delivered to the radiation isocenter, and thus, in some embodiments, the target volume may be placed at the radiation isocenter. Therefore, before the iterative optimization, the radiation isocenter of the therapeutic radiation delivery apparatus 110 may be determined.

In some embodiments, for each section, an initial segment shape and an initial segment MU value may be set before the iterative optimization is performed. For example, in direct aperture optimization (DAO) process, an initial segment shape and an initial segment MU value may be set for each section before the iterative optimization is performed. In some embodiments, a section with an initial segment shape and an initial segment MU value may be also referred to as an initial segment. In some embodiments, the initial segment shape(s) may be selected by initializing leaves of the MLC to be in a specified configuration (e.g., fully open, fully closed, half-open, etc.). In some embodiments, the initial segment shape(s) may be determined by defining a shape of an aperture of the MLC (e.g., round, elliptical, rectangular, etc.) In some embodiments, the initial beam shape(s) may be determined by setting one or more of the segment shapes so that radiation is delivered focusing on the target volume but blocked from healthy tissue or structures. In some embodiments, the initial segment shapes for different sections may be the same. Alternatively, in some embodiments, the initial segment shapes for different sections may be different. For example, the initial segment shape for a first section may be round, while the initial segment shape for a second section may be elliptical.

In some embodiments, a segment MU value may refer to a radiation dose that is delivered in a radiation segment. In some embodiments, the initial segment MU values may be determined by setting one or more of the MU values to zero. In some embodiments, the initial segment MU values may be determined by setting one or more of the MU values to be one or more random values. In some embodiments, the initial segment MU values may be set as a same value. In some embodiments, one or more of the initial segment MU values may be different. For example, the initial segment MU value for a first section may be zero, while the initial segment MU value for a second section may be 100 MU. In some embodiments, the initial segment shapes and the initial segment MU values may be set according to a default setting of the radiation system 100. The initial segment shapes and/or the initial segment MU values may be updated or optimized during the iterative optimization. In some embodiments, in a DAO process, the plurality of radiation segments may be determined based on direct optimization of angle ranges, segment shapes, and segment MU values of the plurality of radiation segments in an iterative optimizing operation.

It should be noted that in some embodiments (e.g., in a fluence map optimization [FMO] process), the initial segment shapes and/or the initial segment MU values may not be assigned an initial shape or value before iterative optimization, and segment shapes and/or segment MU values may be directly determined during the iterative optimization. In some embodiments, the plurality of radiation segments may be determined based on the plurality of sections determined in 603 during the iterative optimization. In some embodiments, for each section, a fluence map may be determined by iteratively optimizing the dose distribution relative to the set of one or more optimization goals. The fluence map may correspond to a plurality of angles within an angle range of the each section. In some embodiments, the plurality of fluence maps may be decomposed. In some embodiments, the plurality of radiation segments may be determined based on the plurality of decomposed fluence maps. Specifically, for each section, the segment determination unit 506 may divide a whole radiation field of the each section into a plurality of sub-fields. In some embodiments, the segment determination unit 506 may determine a sub-field segment based on each sub-field. In some embodiments, the sub-field segment may have a segment shape that is the same as the each sub-field. In some embodiments, the sub-field segment may have an angle range that is the same as or smaller than the each section. In some embodiments, the sub-field segment may have a unit beam intensity (e.g., 1 MU).

Merely by way of example, in the FMO process, the segment determination unit 506 may determine a fluence map by iteratively optimizing the dose distribution relative to the set of one or more optimization goals. In some embodiments, a fluence map may represent a desired intensity profile of beams that are planned to be delivered to a target volume of a subject in radiation therapy. The fluence map may include a plurality of elements. Each element of the fluence map may represent an MU value of a sub-field segment. The segment determination unit 506 may determine the plurality of radiation segments based on the determined fluence map. For example, the segment determination unit 506 may determine a segment count of the plurality of radiation segments, an angle range of each of the plurality of radiation segments, one or more segment shapes of each of the plurality of radiation segments, one or more segment MU rates of each of the plurality of radiation segments, and/or one or more segment MU values of each of the plurality of radiation segments. In some embodiments, the segment determination unit 506 may adjust the sub-field segments to determine the plurality of radiation segments based on the fluence map.

In some embodiments, the iterative optimization may be performed based on the plurality of sections determined in 603, the initial segment shapes, and/or the initial segment MU values. In the iterative optimization, desirable segment shapes, segment MU values, and/or radiation segments may be determined. In some embodiments, one or more iterations may be performed in iterative optimization until a dose distribution satisfies the optimization goals. In some embodiments, the dose distribution may refer to a three-dimensional (3D) or two-dimensional (2D) distribution of radiation dose delivered to a plurality of voxels associated with the subject (e.g., a target volume, a volume surrounding the target volume, or the like, or any combination thereof). In the first iteration, a plurality of radiation segments and the corresponding angle ranges, segment shapes and segment MU values may be determined. In the other iterations, the radiation segments and the corresponding angle ranges, segment shapes, and segment MU values may be updated, and accordingly, a dose distribution may be determined based on the updated radiation segments, and updated angle ranges, updated segment shapes, and updated segment MU values of the updated radiation segments, and then a characteristic value indicating how closely the dose distribution satisfies the optimization goals may be determined. In some embodiments, the iteration may be terminated until one or more conditions are satisfied. An exemplary condition may be associated with whether the characteristic value reaches or exceeds a threshold, whether the difference between two dose distributions determined in two or more consecutive iterations is equal to or less than a threshold, whether a specified number of iterations are performed, or the like, or a combination thereof.

In some embodiments, the dose distribution may be optimized relative to the set of one or more optimization goals according to one or more iterative optimization algorithms. Exemplary iterative optimization algorithms may include a simulated annealing (SA) algorithm, an algebraic inverse treatment planning (AITP) algorithm, a simultaneous iterative inverse treatment planning (SIITP) algorithm, a Monte Carlo (MC) algorithm, a pencil beam convolution (PBC) algorithm, a gradient-based algorithm (e.g., a conjugate gradient algorithm, a Quasi-Newton algorithm), a genetic algorithm, a neural network-based algorithm, or the like, or any combination thereof. In some embodiments, one or more iterative optimization algorithms may be used in the iterations. For example, in a first portion of the iterations (e.g., the $1^{st}$-$N^{th}$, iterations), a simulated annealing algorithm may be used, while in a second portion of the iterations (e.g., the $(N+1)^{th}$-$M^{th}$ iterations, with M>N), a gradient-based algorithm may be used. According to the iterative optimization process, a plurality of (desired) radiation segments may be determined, and an angle range, one or more segment shapes, and one or more segment MU values for each radiation segment may be determined.

It should be noted that in some embodiments, the dose distribution may be iteratively optimized relative to the optimization goals based on one or more constraints associated with the therapeutic radiation delivery apparatus 110. The constraints associated with the therapeutic radiation delivery apparatus may include one or more physical limitations of the therapeutic radiation delivery apparatus, for example, a maximal MU rate of the radiation source, a maximal rotation speed of the radiation source, a minimal rotation speed of the radiation source, an acceleration time of the radiation source, a deceleration time of the radiation source, a maximal acceleration of the radiation source, a maximal jerk of the radiation source, a deceleration velocity of the radiation source, a maximal leaf speed of a multi-leaf collimator (MLC) of the therapeutic radiation delivery apparatus, a motion range of multiple leaves of the MLC, a maximal leaf acceleration of the MLC, a maximal leaf jerk of the MLC, or the like, or any combination thereof. In some embodiments, the MU rate of the radiation source may be within a range of 0-5000 MU/min. In some embodiments, the MU rate of the radiation source may be within a range of 100-5000 MU/min. In some embodiments, the MU rate of the radiation source may be within a range of 1400-1800 MU/min. For example, the segment shapes may be limited by the structure and/or available maneuver of the MLC. As another example, the segment MU values may be limited by an MU rate and a rotation speed of the radiation source.

In some embodiments, the number of radiation segments (or referred to as the segment count) may be increased or reduced relative to the sections. For example, 40 radiation segments may be generated based on 15 sections after the iterative optimization. As another example, 10 radiation segments may be generated based on 15 sections after the iterative optimization. Alternatively, or additionally, the angle ranges of one or more of the radiation segments may be different from their respective sections, as exemplified in FIGS. 8A and 8B.

Figure 8A:
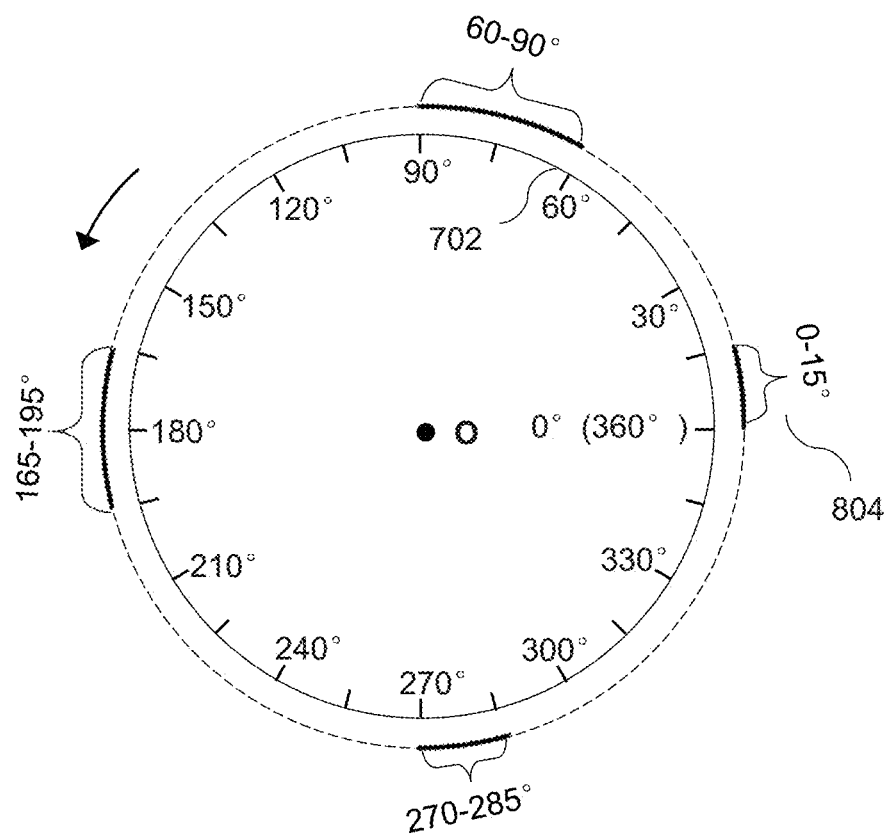
FIGS. 8A and 8B are schematic diagrams illustrating exemplary radiation segments according to some embodiments of the present disclosure.
Figure 8B:
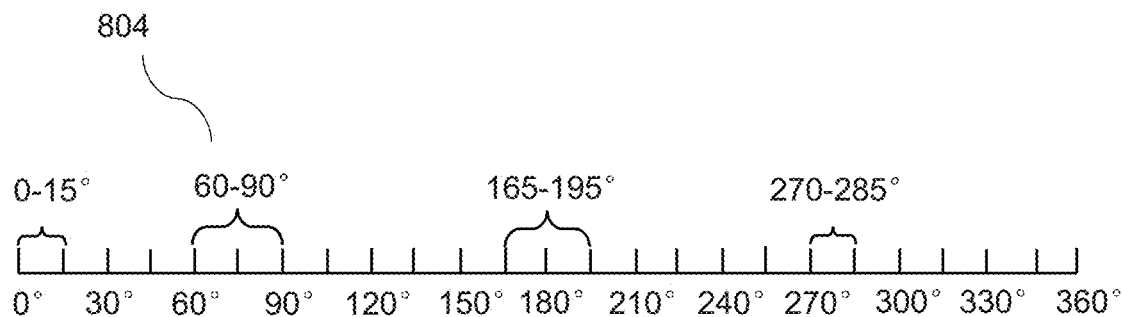

FIGS. 8A and 8B are schematic diagrams illustrating exemplary radiation segments according to some embodiments of the present disclosure. As illustrated in FIG. 8A, the rotary ring 702 may rotate around the rotation center O clockwise or counterclockwise. One or more radiation segments 804 are distributed on the rotary ring 702. The exemplary radiation segments 804 may correspond to angle ranges 0°-15°, 60°-90°, 165°-195°, and 270°-285°. Merely for illustration purposes, the radiation segment(s) 804 may be expressed on a straight line section that represents the rotation range of 0°-360°, as shown in FIG. 8B. Compared with the sections 704, the number and angle range(s) of the radiation segments 804 may be different. Specifically, 4 radiation segments may be generated based on 6 sections after the iterative optimization. The radiation segments 804 may be unevenly distributed on the rotary ring 702. In some embodiments, the span of two of the radiation segments may be different or the same. For example, the span of a first radiation segment may be 15° (e.g., an angle range of 0°-15° as shown in FIGS. 8A and 8B), while the span of a second radiation segment may be 30° (e.g., an angle range of 60°-90° as shown in FIGS. 8A and 8B). As another example, the span of a first radiation segment may be 15° (e.g., an angle range of 0°-15° as shown in FIGS. 8A and 8B), and the span of a third radiation segment may also be 15° (e.g., an angle range of 270°-285° as shown in FIGS. 8A and 8B). In some embodiments, the angle range of a first radiation segment may at least partially overlap with the angle range of a second radiation segment. For example, the angle range of the first radiation segment may be 30°-50°, while the angle range of the second radiation segment may be 40°-70°. In some embodiments, the angle range of a first radiation segment may include the angle range of a second radiation segment. For example, the angle range of the first radiation segment may be 50°-100°, while the angle range of the second radiation segment may be 60°-90°. It should be noted that the above descriptions of the radiation segments 804 is merely provided for the purposes of illustration and not intended to limit the scope of the present disclosure.

The segment shapes and/or the segment MU values for different radiation segments may be the same or different. In some embodiments, the plurality of radiation segments may have multiple angle ranges. Each angle range of the multiple angle ranges may correspond to one or more segment shapes and one or more segment MU values. In some embodiments, a first radiation segment and a second radiation segment of the plurality of radiation segments may have a same angle range, but have different segment shapes, different segment MU rates, and/or different segment MU values. Merely by way of example, the first radiation segment and the second radiation segment may have the same angle range 0°-20°, the first radiation segment may have a first segment shape and a first MU value, while the second radiation segment may have a second segment shape (that is different from the first segment shape) and a second MU value (that is different from the first MU value).

Figure 10:
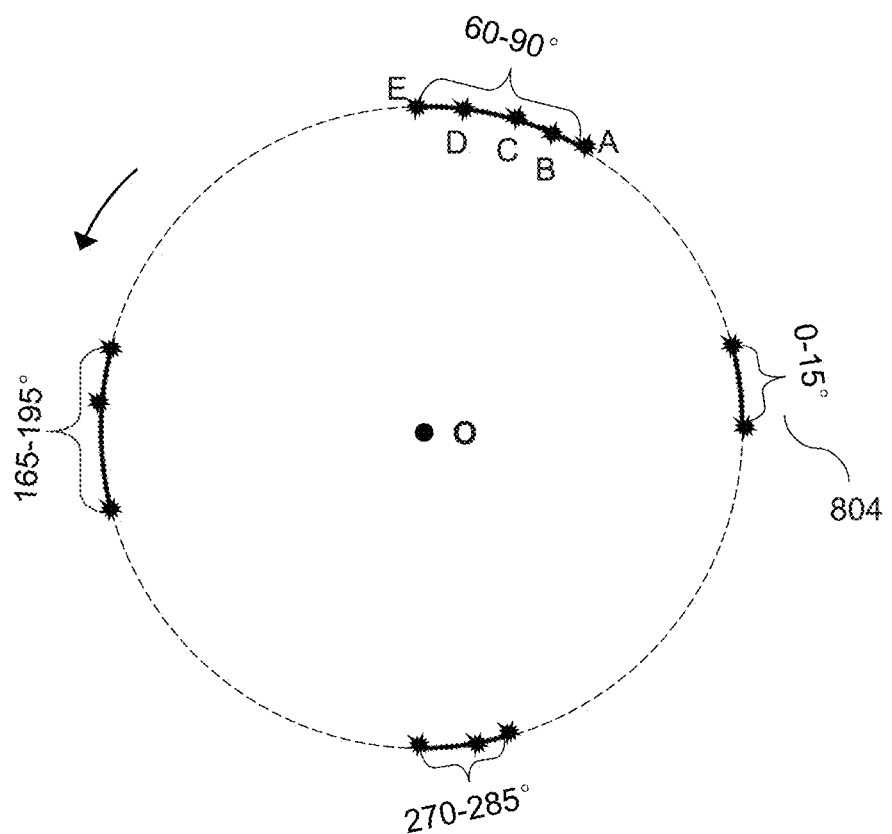
FIG. 10 is a schematic diagram illustrating exemplary control points and exemplary sub-segments according to some embodiments of the present disclosure.

In some embodiments, during the iterative optimization (e.g., in at least one iteration of the iterative optimization process), the segment determination unit 506 may determine, in at least one iteration, a plurality of sub-segments of at least one radiation segment of the plurality of radiation segments based on one or more control points. In some embodiments, the control points may be determined according to the iterative optimization algorithm(s) described elsewhere in the present disclosure. In some embodiments, a radiation segment may include one or more control points, which may define the starting points and/or ending points of the sub-segments. The control points in two different radiation segments may be different. For example, a first radiation segment may have two control points (e.g., the radiation segment corresponding to the angle range 0°-15° as shown in FIG. 10), while a second radiation segment may have five control points (e.g., the radiation segment corresponding to the angle range 60°-90° as shown in FIG. 10). FIG. 10 is a schematic diagram illustrating exemplary control points and exemplary sub-segments according to some embodiments of the present disclosure.

Merely by way of example, a radiation segment corresponding to the angle range 60°-90° may include five control points; that is, control point A, control point B, control point C, control point D, and control point E. Four sub-segments may be determined based on the five control points. In some embodiments, control point A may be a starting point of a first sub-segment (or the starting point of the corresponding radiation segment). Control point B may be an ending point of the first sub-segment and a starting point of a second sub-segment. Similarly, control point C may be an ending point of the second sub-segment and a starting point of a third sub-segment. Control point D may be an ending point of the third sub-segment and a starting point of a fourth sub-segment. Control point E may be an ending point of the fourth sub-segment (or the ending point of the corresponding radiation segment). It should be noted that the above description of the control points is merely provided for the purposes of illustration and not intended to limit the scope of the present disclosure.

In some embodiments, for radiation delivery, the first radiation source 114 may continuously emit radiation beams in the plurality of sub-segments, but the segment shapes and the MU values of two sub-segments may be different.

In some embodiments, the segment shape(s) may be limited by the MLC of the therapeutic radiation delivery apparatus 110. The MLC may include multiple movable leaves, and the MLC may be rotated relative to the first radiation source 114. Thus, the segment determination unit 506 may determine, in at least one iteration, a collimator angle of the MLC of the therapeutic radiation delivery apparatus 110 and a segment shape for each control point of the one or more control points. In some embodiments, a first collimator angle of the MLC for a first control point may be different from a second collimator angle of the MLC for a second control point. In some embodiments, a first segment shape for the first control point may be different from a second segment shape for the second control point. In some embodiments, the positions of the multiple leaves of the MLC may be adjusted so that the first segment shape at the first control point may change gradually to become the second segment shape at the second control point. The segment determination unit 506 may also determine, in at least one iteration, an MU value for each sub-segment of the plurality of sub-segments. In some embodiments, the MU value may be determined based on a rotation speed and an MU rate of the first radiation source 114. In some embodiments, as the rotation speed may be predetermined, the MU value may be determined by adjusting the MU rate of the first radiation source 114. In some embodiments, a first MU value of a first sub-segment may be different from a second MU value of a second sub-segment. In some embodiments, the segment determination unit 506 may further iteratively optimize the dose distribution relative to the set of one or more optimization goals based on the plurality of sub-segments and the plurality of radiation segments excluding the at least one radiation segment that has the plurality of sub-segments.

In 607, the processing device 140 (e.g., the delivery trajectory determination unit 508) may determine a sequence of the plurality of radiation segments for radiation delivery to obtain a delivery trajectory of the radiation source of the therapeutic radiation delivery apparatus. In some embodiments, a radiation treatment plan may become complete when the delivery trajectory is determined. In some embodiments, the processing device 140 may determine the radiation treatment plan based on the plurality of sequential radiation segments for radiation delivery and the delivery trajectory of the radiation source of the therapeutic radiation delivery apparatus. In some embodiments, the processing device 140 may provide the radiation treatment plan including the plurality of sequential radiation segments for radiation delivery and the delivery trajectory of the radiation source of the therapeutic radiation delivery apparatus. In some embodiments, the delivery trajectory may include a plurality of radiation segments, and each radiation segment may have one or more segment shapes, and one or more segment MU values. In some embodiments, a radiation segment may include a plurality of sub-segments, each sub-segment may have an angle range, one or more segment shapes and a segment MU value.

In some embodiments, the processing device 140 (e.g., the delivery trajectory determination unit 508) may determine the delivery trajectory of the radiation source (e.g., the first radiation source 114) based on the plurality of radiation segments and one or more constraints associated with the therapeutic radiation delivery apparatus 110. The constraints associated with the therapeutic radiation delivery apparatus may include one or more physical limitations of the therapeutic radiation delivery apparatus, for example, a maximal MU rate of the radiation source, a maximal rotation speed of the radiation source, a minimal rotation speed of the radiation source, an acceleration time of the radiation source, a deceleration time of the radiation source, a maximal acceleration of the radiation source, a maximal jerk of the radiation source, a deceleration velocity of the radiation source, a maximal leaf speed of a multi-leaf collimator (MLC) of the therapeutic radiation delivery apparatus, a motion range of multiple leaves of the MLC, a maximal leaf acceleration of the MLC, a maximal leaf jerk of the MLC, or the like, or any combination thereof. In some embodiments, the MU rate of the radiation source may be within a range of 0-5000 MU/min. In some embodiments, the MU rate of the radiation source may be within a range of 100-5000 MU/min. In some embodiments, the MU rate of the radiation source may be within a range of 1400-1800 MU/min.

It should be noted that a segment MU value may be determined based on a rotation speed and an MU rate of the first radiation source 114. As the rotation speed of the first radiation source 114 may be relatively fast and the MU rate of the first radiation source 114 may be confined by the physical limitations of the therapeutic radiation delivery apparatus 110, the segment MU value corresponding to a radiation segment may be limited. Therefore, if a relatively high segment MU value needs to be delivered during a radiation segment, the segment MU value of the radiation segment may need to be distributed in two or more different rotations (see FIG. 9C). In some embodiments, a relatively high MU rate may be applied in radiation therapy, so that the number of rotations may be reduced, and the time for radiation therapy may be reduced.

As illustrated above, in some embodiments, the delivery trajectory may include multiple rotations. In some embodiments, the plurality of radiation segments may be distributed in the multiple rotations. In some embodiments, the segment MU value of a radiation segment may be delivered or distributed in one or more rotations. In some embodiments, a rotation may include one or more radiation segments. For instance, the first rotation of the plurality of rotations may include one or more first radiation segments, and a second rotation of the plurality of rotations may include one or more second radiation segments. In some embodiments, one of the first radiation segments and one of the second radiation segments may have different angle ranges. Alternatively, one of the first radiation segments may have a first angle range, one of the second radiation segments may have a second angle range, and the first angle range and the second angle range may at least partially overlap.

Figure 9A:
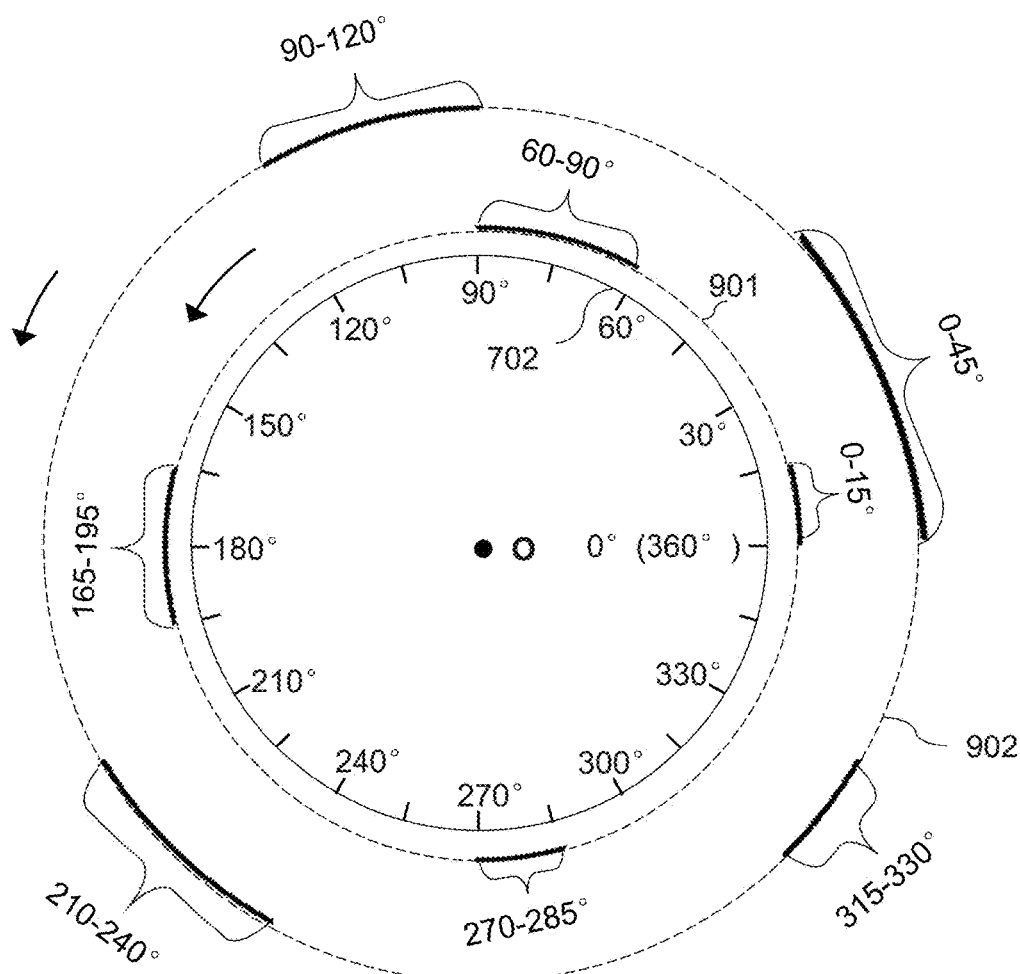
FIGS. 9A and 9B are schematic diagrams illustrating an exemplary delivery trajectory according to some embodiments of the present disclosure.
Figure 9B:
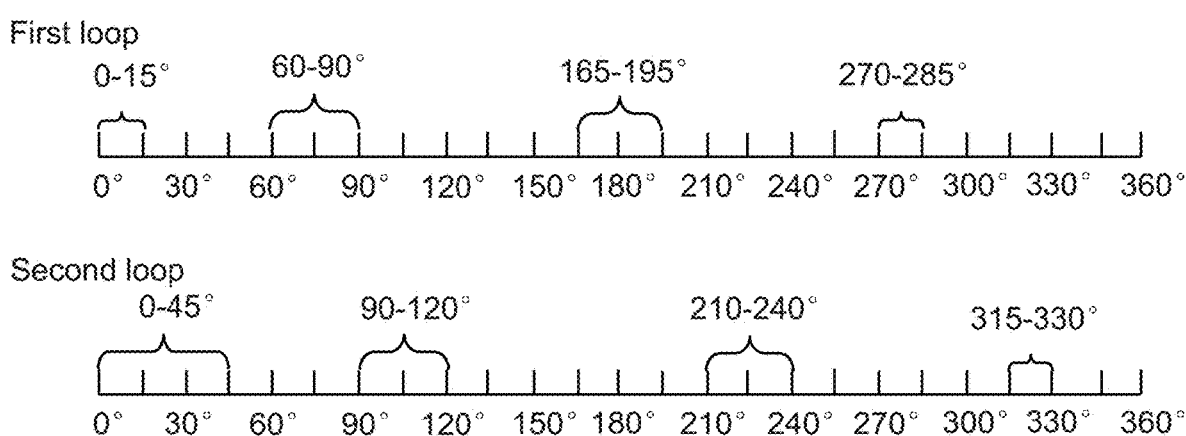

Alternatively, one of the first radiation segments and one of the second radiation segments may have a same angle range, but different segment shapes, different segment MU rates, and/or different segment MU values. Alternatively, one of the first radiation segments and one of the second radiation segments may have a same angle range, a same segment shape, a same segment MU rate, and/or a same segment MU value. In some embodiments, during one or more of the plurality of rotations, no radiation may be delivered. In some embodiments, at least one first radiation segment of the first rotation may be different from at least one second radiation segment of the second rotation (see FIGS. 9A and 9B). FIGS. 9A and 9B are schematic diagrams illustrating an exemplary delivery trajectory according to some embodiments of the present disclosure. As shown in FIG. 9A, the delivery trajectory may include a first rotation 901 and a second rotation 902, and the plurality of radiation segments may correspond to angle ranges 0°-15°, 0°-45°, 60°-90°, 90°-120°, 165°-195°, 210°-240°, 270°-285°, and 315°-330°. Merely for illustration purposes, the first rotation and second rotation of the delivery trajectory may be expressed on a straight line section that represents the rotation range of 0°-360°, as shown in FIG. 9B. In some embodiments, the segment count and/or angle ranges of the radiation segments of the first rotation 901 may be different from that of the second rotation 902. Specifically, four radiation segments corresponding to angle ranges 0-15°, 60-90°, 165-195°, and 270-285° may be distributed in the first rotation 901, while four radiation segments corresponding to angle ranges 0-45°, 90-120°, 210-240°, and 315-330° may be distributed in the second rotation 902. It should be noted that the size of the circle 901 is shown different from the size of the circle 902 in FIG. 9A so that the first rotation may be distinguished from the second rotation in the drawings and does not suggest that the delivery trajectory during the first rotation and the delivery trajectory during the second rotation are different in size. It should be noted the above descriptions of the delivery trajectory is merely an example and not intended to limit the scope of the present disclosure.

Figure 9C:
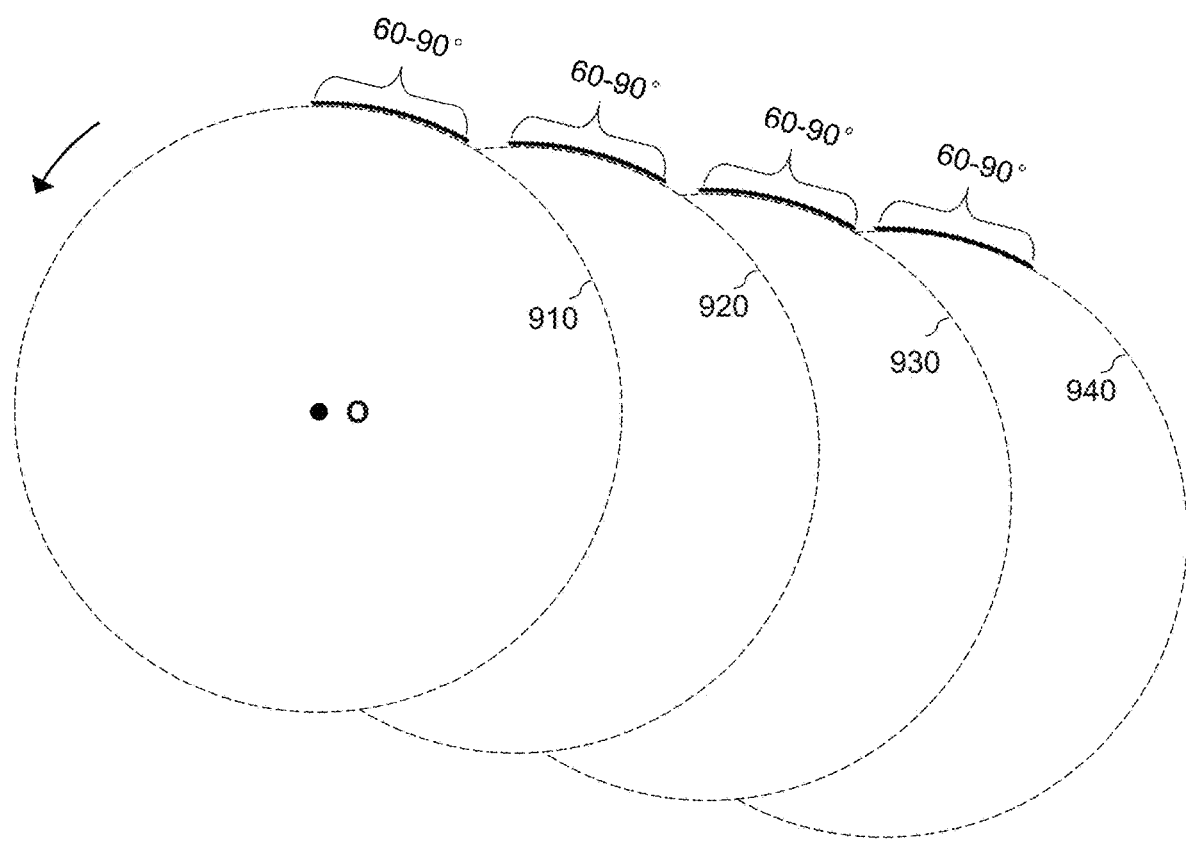
FIG. 9C is a schematic diagram illustrating an exemplary segment MU value of an exemplary radiation segment distributed in multiple rotations according to some embodiments of the present disclosure.

In some embodiments, at least one portion of a segment MU value of a radiation segment of the plurality of radiation segments may be distributed in at least two rotations of the plurality of rotations (see FIG. 9C). In some embodiments, the segment MU value may be uniformly distributed along the rotations. In some embodiments, the segment MU value may be randomly distributed along the rotations so that the MU value distributed along each rotation may fall within a threshold. In some embodiments, the threshold may relate to an MU rate of the first radiation source 114 and/or a rotation speed of the first radiation source 114. FIG. 9C is a schematic diagram illustrating an exemplary segment MU value of an exemplary radiation segment distributed in multiple rotations according to some embodiments of the present disclosure. As shown in FIG. 9C, the radiation segment S may have the angle range 60°-90°. The radiation segment S may have a segment MU value D. In some embodiments, the rotation speed of the radiation source is relatively high, and the radiation time in the radiation segment S is relatively short, and thus the segment MU value D may not be delivered in a single rotation. In FIG. 9C, the segment MU value D may be distributed over four rotations of a delivery trajectory, namely, a first rotation 910, a second rotation 920, a third rotation 930, and a fourth rotation 940. In some embodiments, the MU value distributed over the four rotations may be substantially the same (e.g., approximately D/4).

It should be noted that the above description of the process 600 is provided for the purposes of illustration, and is not intended to limit the scope of the present disclosure. For persons having ordinary skills in the art, multiple variations and modifications may be made under the teachings of the present disclosure. However, those variations and modifications do not depart from the scope of the present disclosure. For example, operations 603 and 605 may be integrated into a single operation. As another example, the delivery trajectory determined in 607 may be stored in a storage device (e.g., the storage device 150) for further use.

In some embodiments, one or more imaging protocols that are to be executed during radiation therapy, an execution interval of the one or more imaging protocols, and/or an execution sequence of the one or more imaging protocols may be obtained by, for example, the acquisition module 404. In some embodiments, the dose distribution may be iteratively optimized relative to the optimization goals based on one or more constraints associated with the therapeutic radiation delivery apparatus and/or the one or more imaging protocols. In some embodiments, the generated radiation treatment plan may be adjusted based on the one or more imaging protocols. Merely by way of example, the one or more imaging protocols may indicate that during radiation therapy, 10 slices of CT images may need to be generated to monitor a movement of a tumor. Then the radiation treatment plan may be adjusted accordingly. Specifically, it may be planned that the first radiation source 114 does not deliver radiation during the CT scanning. That is, a plurality of rotations including no radiation delivery may be added between a first rotation prior to the CT scanning and a second rotation after the CT scanning, and accordingly, the execution time for radiation delivery in a radiation segment of the second rotation may be delayed.

In some embodiments, a set of one or more optimization goals for radiation delivery by a therapeutic radiation delivery apparatus may be obtained. In some embodiments, one or more imaging protocols that are to be executed during radiation therapy may be obtained. In some embodiments, one or more radiation delivery parameters associated with the radiation treatment plan may be determined by iteratively optimizing a dose distribution relative to the set of one or more optimization goals. In some embodiments, the radiation treatment plan may include a 3D imaging plan associated with the one or more imaging protocols to be executed during radiation therapy. In some embodiments, a sequence of radiation segments of the radiation treatment plan may be determined based on one or more images generated according the 3D imaging plan. In some embodiments, the one or more radiation delivery parameters may include a plurality of radiation segments and/or an execution sequence of the plurality of radiation segments. In some embodiments, the one or more radiation delivery parameters associated with the radiation treatment plan may be determined based on the set of one or more optimization goals and/or the one or more imaging protocols. In some embodiments, radiation delivery and at least one of the one or more imaging protocols may be planned to be executed synchronously in at least one period of time according to the radiation treatment plan and the 3D imaging plan. In some embodiments, radiation delivery and at least one of the one or more imaging protocols may be planned to be executed asynchronously in at least one period of time according to the radiation treatment plan and the 3D imaging plan.

In some embodiments, a radiation treatment plan including a delivery trajectory of a radiation source of a therapeutic radiation delivery apparatus may be obtained. In some embodiments, one or more imaging protocols that are to be executed during radiation therapy may be obtained. In some embodiments, the radiation treatment plan may be adjusted based on the one or more imaging protocols. In some embodiments, a treatment radiation beam may be delivered from the radiation source to the target volume according to the adjusted radiation treatment plan. In some embodiments, the adjusted radiation treatment plan may include a 3D imaging plan associated with the one or more imaging protocols to be executed during radiation therapy. In some embodiments, the delivery trajectory may include a plurality of radiation segments and/or an execution sequence of the plurality of radiation segments. In some embodiments, the delivery trajectory may include a plurality of rotations. In some embodiments, the radiation treatment plan may be adjusted based on the one or more imaging protocols.

In some embodiments, an imaging protocol may include an acquisition protocol and/or a reconstruction protocol. The acquisition protocol may include information relating to a voltage of a tube of an imaging radiation source (e.g., the second radiation source 113), a current of the tube of the imaging radiation source, the type of a focal spot of the imaging radiation source, a size of the focal spot of the imaging radiation source, a collimation width of the imaging radiation source (e.g., 0.5 mm, 1 mm, 10 mm, 20 mm, 40 mm, 50 mm, etc.), the type of a bowtie filter of the imaging radiation source, a shot number of the imaging radiation source, a view number of a detector (e.g., a detector (also referred to as radiation detector) of the detector module 112), a time of one revolution of a gantry (e.g., the gantry 111), a tilt angle of the gantry, one or more body parts of the subject to be scanned, a movement direction of a table (e.g., the table 115), position information of the subject (e.g., a supine position, a prone position, a decubitus right position, a decubitus left position, etc.), a scanning mode (e.g., a helical scanning, an axial scanning), a pitch, whether to use a digital orthophoto map (DOM), or the like, or a combination thereof. The reconstruction protocol may include information relating to a reconstruction center, a reconstruction field of view (FOV), a filtering or kernel function, an intensity viewing window level, an intensity viewing window width, an image thickness, an image increment, an image resolution (e.g., 512×512), a noise level of the image, or the like, or a combination thereof.

In some embodiments, a radiation treatment plan may be adjusted based on one or more imaging protocols by adjusting an angle range of a radiation segment, a segment shape of a radiation segment, a segment MU value of a radiation segment, a segment MU rate of a radiation segment, a sub-segment of a radiation segment, and/or an execution sequence of the plurality of radiation segments (and/or sub-segments), increasing a time for radiation therapy, delaying a time for radiation delivery in a radiation segment, adding an imaging plan (e.g., a 3D imaging plan) associated with the one or more imaging protocols to the radiation treatment plan, adding one or more rotations including no radiation delivery between a first radiation segment of the plurality of radiation segments and a second radiation segment of the plurality of radiation segments, or the like, or any combination thereof.

Figure 11:
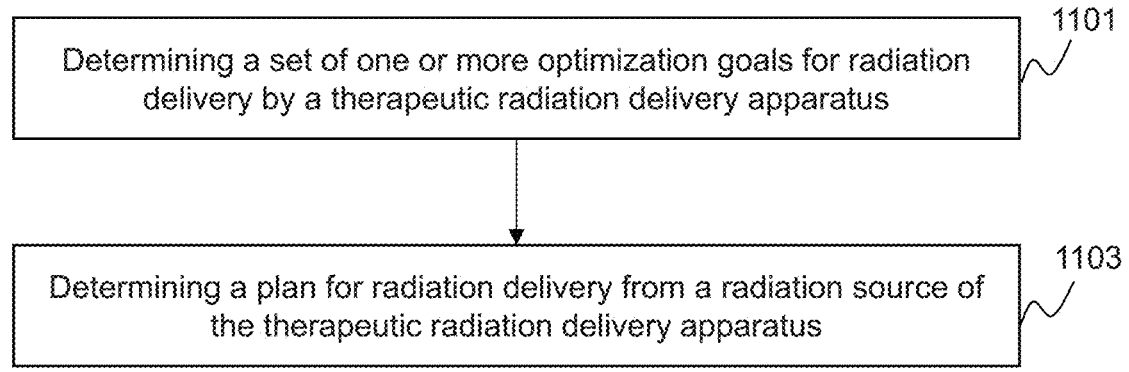
FIG. 11 is a flowchart illustrating an exemplary process for determining a radiation treatment plan according to some embodiments of the present disclosure.

FIG. 11 is a flowchart illustrating an exemplary process for determining a radiation treatment plan according to some embodiments of the present disclosure. In some embodiments, one or more operations of process 1100 illustrated in FIG. 11 may be performed by the processing device 140 (e.g., the plan generation module 402). In some embodiments, one or more operations of process 1100 may be implemented in the radiation system 100 illustrated in FIG. 1. For example, the process 1100 may be stored in the storage device 150 and/or the storage 220 in the form of instructions (e.g., an application), and invoked and/or executed by the processing device 140 (e.g., the processor 210 of the computing device 200 as illustrated in FIG. 2, the CPU 340 of the mobile device 300 as illustrated in FIG. 3, one or more modules of the processing device 140 as illustrated in FIG. 4, one or more units of the plan generation module 402 as illustrated in FIG. 5, or the like). As another example, a portion of the process 1100 may be implemented on the therapeutic radiation delivery apparatus 110. The operations of the illustrated process presented below are intended to be illustrative. In some embodiments, the process 1100 may be accomplished with one or more additional operations not described, and/or without one or more of the operations discussed. Additionally, the order in which the operations of the process 1100 as illustrated in FIG. 11 and described below is not intended to be limiting.

In 1101, the processing device 140 (e.g., the optimization goal determination unit 502) may determine a set of one or more optimization goals for radiation delivery by a therapeutic radiation delivery apparatus (e.g., the therapeutic radiation delivery apparatus 110). In some embodiments, the set of one or more optimization goals may relate to one or more dose constraints, one or more target volumes (e.g., the geometry of the target volumes, the position of the target volumes), one or more structures outside of the target volume(s) (e.g., the geometry of the structures, the position of the target volumes), the delivery time, etc. More descriptions regarding the optimization goal(s) may be found elsewhere in the present disclosure (e.g., operation 601 of process 600 and the relevant descriptions thereof).

In 1103, the processing device 140 (e.g., the plan generation module 402) may determine a plan for radiation delivery (also referred to herein as radiation treatment plan) from a radiation source (e.g., the first radiation source 114) of the therapeutic radiation delivery apparatus. In some embodiments, the radiation source may be capable of continuously rotating around a subject in one direction (e.g., a clockwise direction, a counterclockwise direction). The plan may include a plurality of radiation segments. In some embodiments, each radiation segment may be characterized by at least one parameter selected from a start angle, a stop angle, a 2D segment shape, and/or a radiation dose (also referred to herein as a segment MU value). In some embodiments, the plurality of radiation segments may be optimized to meet the set of one or more optimization goals by superimposing at least two radiation segments from at least two different rotations into a target volume of the subject. A start angle may refer to a position where radiation delivery starts while the radiation source is in continuous rotation. A stop angle may refer to a position where radiation delivery stops while the radiation source is in continuous rotation. For example, the radiation segment 804 corresponding to the angle range 60°-90° may have a start angle 60° and a stop angle 90°. It should be noted that the start angle and the stop angle in the present disclosure may be different from that in traditional arc therapy.

In some embodiments, the radiation segments in different rotations may have the same or different segment shape(s) and/or segment MU value(s). In some embodiments, two or more radiation segments in a same rotation may have the same or different segment shape(s) and/or segment MU value(s). For example, two consecutive radiation segments in a same rotation may have the same segment shape and/or the same segment MU value. As another example, a first radiation segment in a first rotation and a second radiation segment in a second rotation may have different segment shapes and/or segment MU values. In some embodiments, a start angle and a stop angle of a radiation segment may define an angle range of the radiation segment. In some embodiments, two or more of the plurality of radiation segments in the radiation treatment plan may have the same or different angle ranges.

In some embodiments, a radiation segment MU rate of a radiation segment (e.g., each radiation segment) to be delivered between the start angle and the stop angle of the (each) radiation segment may be substantially constant. Alternatively or additionally, the radiation segment MU rate of a radiation segment (e.g., each radiation segment) to be delivered between the start angle and the stop angle of the (each) radiation segment may be variable. In some embodiments, the radiation segment MU rate may be optimized at a plurality of angles between the start angle and stop angle of the (each) radiation segment to achieve the set of one or more optimization goals.

In some embodiments, the processing device 140 (e.g., the segment determination unit 506) may determine and/or optimize the plurality of radiation segments by iteratively optimizing a dose distribution relative to the set of one or more optimization goals. In some embodiments, the dose distribution may refer to a 3D or 2D distribution of radiation dose (also referred to herein as MU value) delivered to a plurality of voxels associated with the subject (e.g., a target volume, a volume surrounding the target volume, or the like, or any combination thereof). In some embodiments, one or more iterations may be performed in iterative optimization until a dose distribution satisfies the optimization goals. It should be noted that in some embodiments, the dose distribution may be iteratively optimized relative to the optimization goals based on one or more constraints associated with the therapeutic radiation delivery apparatus 110. More descriptions regarding the iterative optimization may be found elsewhere in the present disclosure (e.g., operation 605 of process 600 and the relevant descriptions thereof).

In some embodiments, the segment determination unit 506 may optimize the plurality of radiation segments by direct optimization of segment shapes, start angles, stop angles, and segment MU values of the plurality of radiation segments, which is also referred to as a DAO process. In the DAO process, a plurality of initial segments may be determined. Each of the plurality of initial segments may include an initial segment shape, an initial angle range (including an initial start angle and an initial stop angle), an initial segment MU rate, and/or an initial segment MU value. In some embodiments, the initial segments may be set according to a default setting of the radiation system 100 or preset by a user or operator via the terminals 130. The initial segments and/or the segment count of the plurality of radiation segments may be updated during the iterative optimization until optimization criteria associated with the set of one or more optimization goals are met. The optimization criteria may include whether the difference between two dose distributions determined in two or more consecutive iterations is equal to or less than a threshold, whether a specified number of iterations are performed, whether at least two radiation segments are distributed in at least two rotations, or the like, or a combination thereof.

Alternatively, the segment determination unit 506 may optimize the plurality of radiation segments according to an FMO process. In the FMO process, the segment determination unit 506 may generate a fluence map. The fluence map may represent a desired intensity profile of beams that are planned to be delivered to a target volume of a subject in radiation therapy. The fluence map may correspond to a plurality of angles within an angle range of each radiation segment of the plurality of radiation segments. In some embodiments, the fluence map may be generated by iteratively optimizing a dose distribution relative to the set of one or more optimization goals. For example, a plurality of sections of a rotational movement of the radiation source of the therapeutic radiation delivery apparatus may be determined; for each section, a fluence map may be determined by iteratively optimizing the dose distribution relative to the set of one or more optimization goals. More descriptions of the generation of the fluence map may be found elsewhere in the present disclosure (e.g., operation 605 of process 600 and the relevant descriptions thereof). In some embodiments, the segment determination unit 506 may decompose the fluence map to obtain one or more decomposed fluence maps. The segment shapes which are determined by the MLC in different decomposed fluence maps may be different. Each decomposed fluence map may indicate a desired intensity profile of beams that are planned to be delivered to the target volume of the subject in an angle range (e.g., corresponding to a start angle and a stop angle of a radiation segment). The segment determine unit 506 may determine a plurality of radiation segments and an optimized sequence of the plurality of radiation segments based on the one or more decomposed fluence maps and/or the one or more constraints associated with the therapeutic radiation delivery apparatus 110.

In some embodiments, the segment determination unit 506 may optimize a segment count of the plurality of radiation segments to meet the set of one or more optimization goals. For example, the segment determination unit 506 may determine the segment count of the plurality of radiation segments by performing a plurality of iterations. During the plurality of iterations, an estimated segment count may successively increase from a relatively small value until one or more optimization criteria associated with the set of one or more optimization goals are met. When the one or more optimization criteria associated with the set of one or more optimization goals are met, the estimated segment count may be designated as the optimized segment count of the plurality of radiation segments. In some embodiments, a plurality of intermediate segments may be generated in the plurality of iterations. Merely by way of example, $N_1$ intermediate segments may be generated in a first iteration based on $N_0$ initial segments, $N_2$ intermediate segments may be generated in a second iteration based on the $N_1$ intermediate segments, . . . , and finally, $N_m$ radiation segments may be generated in the $m^{th}$ iteration based on the $N_{m-1}$ intermediate segments when the optimization criteria are met (wherein, $N_1 < N_2 < \ldots < N_{m-1} < N_m$). It should be noted that in some embodiments, the segment count of radiation segments may be reduced relative to the initial segments. For example, 10 segments may be generated based on 15 initial segments when the optimization criteria are met. In some embodiments, the processing device 140 (e.g., the delivery trajectory determination unit 508) may determine a sequence to deliver the plurality of radiation segments to obtain a delivery trajectory of the first radiation source 114. The plan for radiation delivery (or the radiation treatment plan) may become complete when the delivery trajectory is determined.

In some embodiments, the plurality of radiation segments may be arranged over at least two different rotations, and at least two radiation segments of the plurality of radiation segments may be at least partially overlapping with each other. The at least two radiation segments overlapping with each other may also be referred to as overlapping segments. In some embodiments, parameters of the plurality of radiation segments may be optimized such that a cumulative dose delivered from the plurality of radiation segments meets the set of one or more optimization goals. In some embodiments, the parameters of the plurality of radiation segments may include the at least one parameter of each radiation segment of the plurality of radiation segments (e.g., starting angles, stop angles, segment shapes, segment MU rates, and/or segment MU values of the plurality of radiation segments). In some embodiments, the plurality of radiation segments may include a first radiation segment in a first rotation of the radiation source and a second radiation segment in a second rotation of the radiation source. A first angle range defined by a first initial start angle and a first initial stop angle may be assigned to the first radiation segment. A second angle range defined by a second initial start angle and a second initial stop angle may be assigned to the second radiation segment. In some embodiments, the first angle range may interleave with the second angle range. In some embodiments, the first radiation segment may be optimized by expanding the first angle range such that the expanded first angle range at least partially overlaps with the second angle range. In some embodiments, at least one of the first initial angle and the first initial stop angle may be modified to expand the first angle range. Alternatively, or additionally, the second radiation segment may be optimized by expanding the second angle range such that the expanded second angle range at least partially overlaps with the first angle range. In some embodiments, at least one of the second initial angle and the second initial stop angle may be modified to expand the second angle range.

Figure 12A:
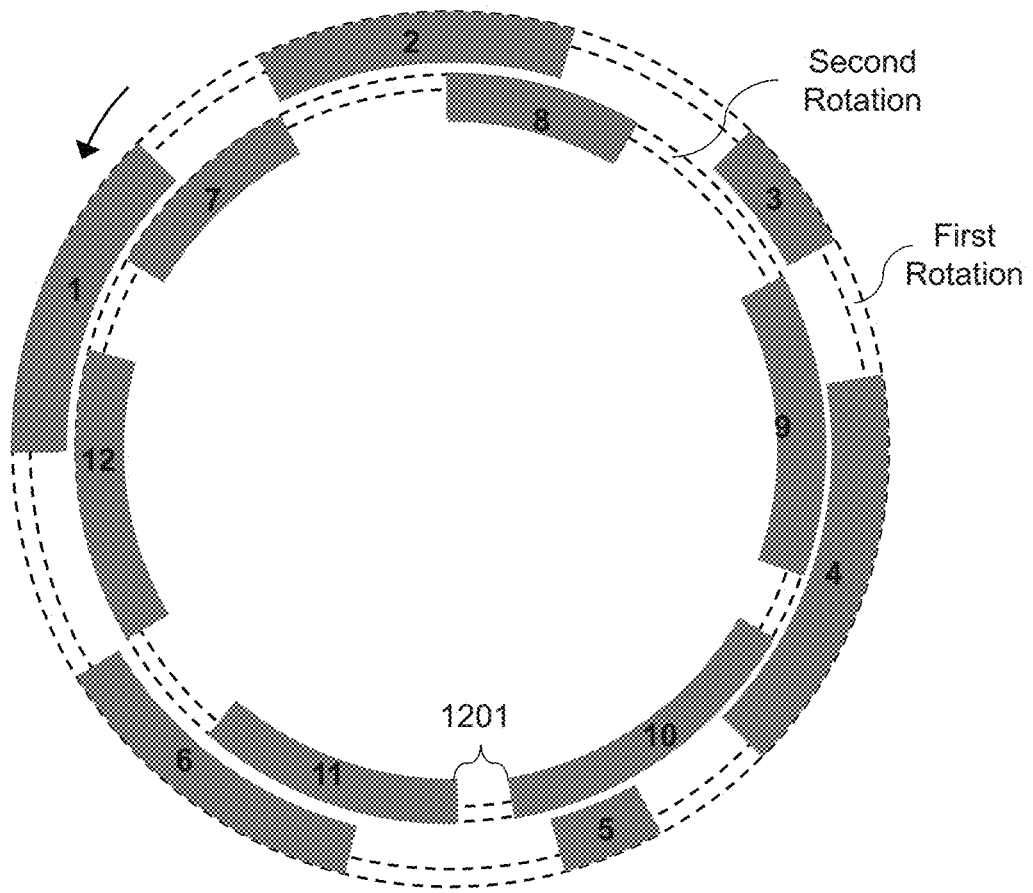
FIG. 12A is a schematic diagram illustrating an exemplary delivery trajectory including two rotations according to some embodiments of the present disclosure.

For the purposes of illustration, FIG. 12A is a schematic diagram illustrating an exemplary delivery trajectory including two rotations according to some embodiments of the present disclosure. As shown in FIG. 12A, the radiation source (e.g., the first radiation source 114) may rotate in a counterclockwise direction. The first rotation may include six radiation segments, i.e., radiation segment 1 to radiation segment 6. The second rotation may include another six radiation segments, i.e., radiation segment 7 to radiation segment 12. In FIG. 12A, at least two radiation segments of the plurality of radiation segments may be at least partially overlapping with each other. For example, radiation segment 1 may be partially overlapping with radiation segment 7. In some embodiments, in addition to the overlapping segments, there may be at least one radiation segment in a rotation interleaving with one or more radiation segments in other rotation(s). For example, as illustrated in FIG. 12A, radiation segment 3 may be interleaving with radiation segment 8 and/or radiation segment 9.

In some embodiments, the plurality of radiation segments may be arranged over at least two rotations of the first radiation source 114 in an interleaving pattern. The radiation segment arranged in an interleaving pattern may also be referred to as interleaved segments. In some embodiments, the start angle(s) and stop angle(s) of one or more (e.g., each) radiation segments of the plurality of radiation segments may be determined according to one or more interleaving patterns. In some embodiments, the interleaving pattern(s) may be set according to a default setting of the radiation system 100 or preset by a user or operator via the terminals 130. Parameters of the plurality of radiation segments may be optimized such that a cumulative dose delivered from the plurality of radiation segments meet the set of one or more optimization goals. The parameters of the plurality of radiation segments may include the at least one parameter of each radiation segment of the plurality of radiation segments.

Figure 12B:
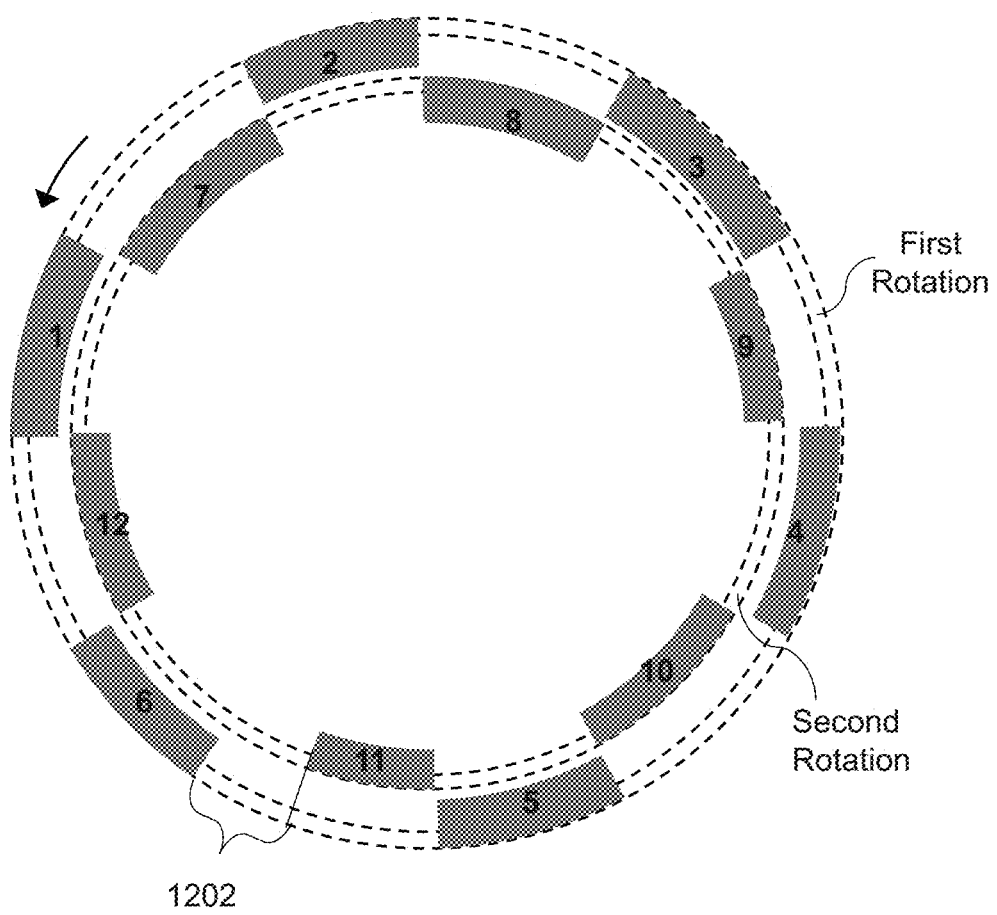
FIG. 12B is a schematic diagram illustrating an exemplary delivery trajectory including two rotations according to some embodiments of the present disclosure.

For the purposes of illustration, FIG. 12B is a schematic diagram illustrating an exemplary delivery trajectory including two rotations according to some embodiments of the present disclosure. As shown in FIG. 12B, the first radiation source 114 may rotate in a counterclockwise direction. The first rotation may include six radiation segments, i.e., radiation segment 1 to radiation segment 6. The second rotation may include another six radiation segments, i.e., radiation segments 7 to 12. In FIG. 12B, the radiation segments in the first rotation and second rotation may be arranged in an interleaving pattern. That is, the radiation segments in the first rotation may interleave with the radiation segments in the second rotation.

In some embodiments, the plurality of radiation segment may include a first set of interleaved radiation segments and a second set of interleaved radiation segments. In some embodiments, the first set of interleaved segments may include one or more radiation segments. In some embodiments, the second set of interleaved segments may include one or more radiation segments. In some embodiments, at least one of the first set of interleaved radiation segments may be at least partially overlapping with at least one of the second sets of interleaved radiation segments.

Figure 12C:
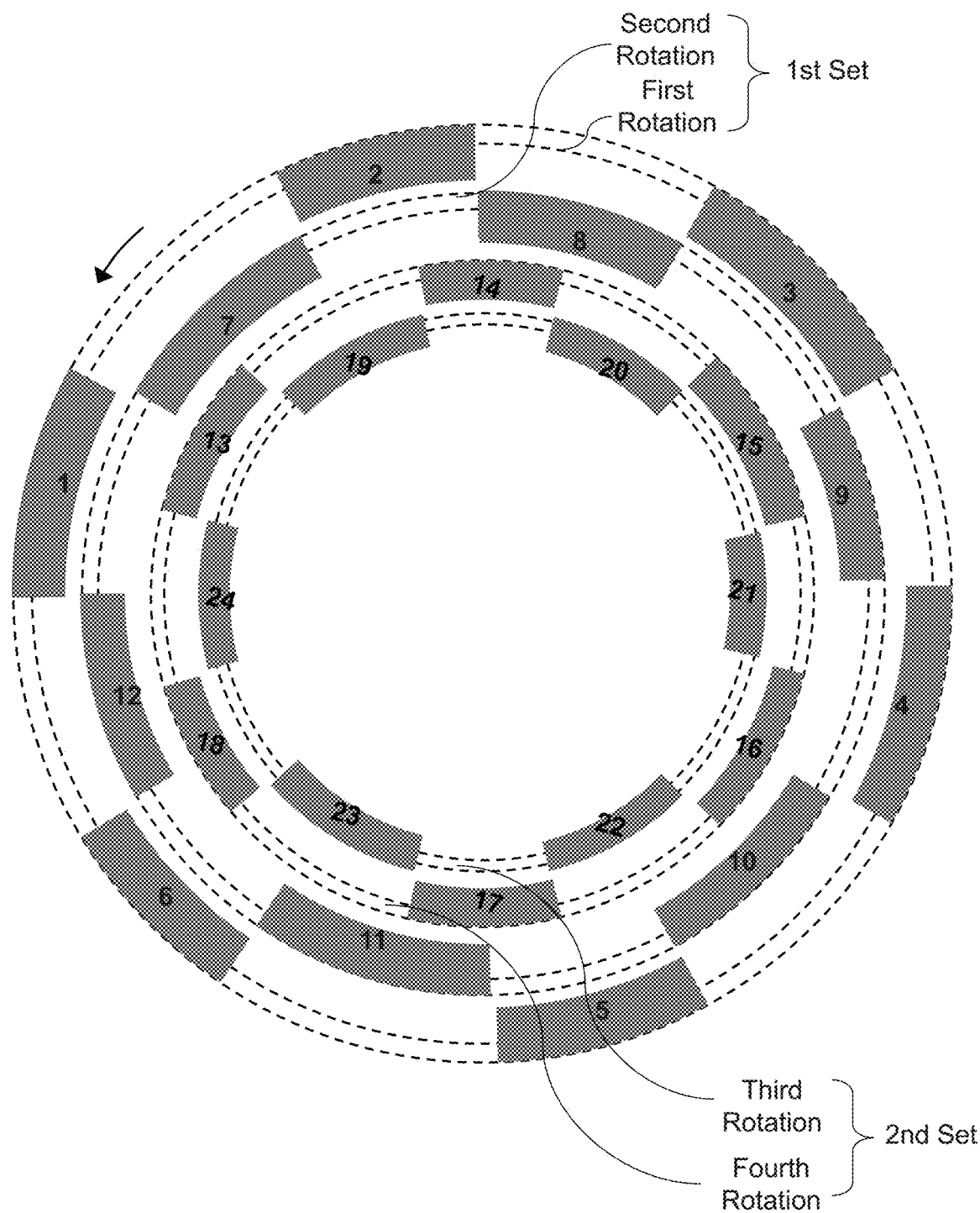
FIG. 12C is a schematic diagram illustrating an exemplary delivery trajectory including four rotations according to some embodiments of the present disclosure.

For the purposes of illustration, FIG. 12C is a schematic diagram illustrating an exemplary delivery trajectory including four rotations according to some embodiments of the present disclosure. As shown in FIG. 12C, the first radiation source 114 may rotate in a counterclockwise direction. The first rotation may include six radiation segments, i.e., radiation segment 1 to radiation segment 6. The second rotation may include six radiation segments, i.e., radiation segment 7 to radiation segment 12. The first set of interleaved segments may include the radiation segments in the first rotation and the second rotation. The third rotation may include six radiation segments, i.e., radiation segment 13 to radiation segment 18. The fourth rotation may include six radiation segments, i.e., radiation segment 19 to radiation segment 24. The second set of interleaved segments may include the radiation segments in the third rotation and the fourth rotation. In FIG. 12C, one or more radiation segments of the first set of interleaved segments may be at least partially overlapping with at least one of the second set of interleaved segments. For example, radiation segment 7 in the second rotation may be at least partially overlapping with radiation segment 13 in the third rotation.

In some embodiments, one or more blank angle ranges (also referred to herein as blank ranges) may exist in the rotations. The blank angle range may refer to an angle range in which no radiation may be delivered. The blank range may include one or more rotations. For example, angle range 1201 in FIG. 12A may be a blank angle range, and angle range 1202 in FIG. 12B may be a blank angle range. In some embodiments, the blank angle ranges between consecutive radiation segments in a same rotation may be uniform or non-uniform. In some embodiments, the blank angle ranges between two interleaving segments in different rotations may be uniform or non-uniform.

It should be noted that the delivery trajectory including two or four rotations illustrated in FIGS. 12A-12C is merely provided for the purpose of illustration, and not intended to limit the scope of the present disclosure. The delivery trajectory may include other numbers of rotations, for example, 3, 5, 10 rotations, or the like. For example, the first set of interleaved segments may only include the first rotation or the second rotation. As another example, the second set of interleaved segments may only include the third rotation or the fourth rotation. The distributions of the radiation segments in the rotations may be various. In some embodiments, the radiation segments may be arranged over two of the rotations in an interleaving pattern. Alternatively, the radiation segments may be arranged over two of the rotations in an overlapping pattern. Alternatively, a portion of the radiation segments may be arranged in an interleaving pattern, and a portion of the radiation segments may be arranged in an overlapping pattern.

It should be noted that the above description of the process 1100 is provided for the purposes of illustration, and is not intended to limit the scope of the present disclosure. For persons having ordinary skills in the art, multiple variations and modifications may be made under the teachings of the present disclosure. However, those variations and modifications do not depart from the scope of the present disclosure. In some embodiments, the processing device 140 may first determine a plurality of sections of a rotational movement of the first radiation source. More descriptions of determination of the sections may be found elsewhere in the present disclosure (e.g., operation 603 of process 600 and the relevant descriptions thereof). A section may correspond to an angle range in which radiation may be delivered during radiation therapy. In some embodiments, the processing device 140 may further determine the plurality of radiation segments (or initial segments) based on the plurality of sections. For example, for each section, the segment determination unit 506 may divide a whole radiation field of the each section into a plurality of sub-fields. In some embodiments, the segment determination unit 506 may determine a sub-field segment based on each sub-field. In some embodiments, the sub-field segment may have a segment shape that is the same as the each sub-field. In some embodiments, the sub-field segment may have an angle range that is the same as or smaller than the each section. In some embodiments, the sub-field segment may have a unit beam intensity (e.g., 1 MU). In some embodiments, one or more imaging protocols that are to be executed during radiation delivery may be obtained. Then the plan for radiation delivery (also referred to herein as radiation treatment plan) from the radiation source may be determined. The plan for radiation delivery may include a 3D imaging plan associated with the one or more imaging protocols.

In summary, the above teachings and exemplary embodiments advance the art of external beam radiation therapy by describing how to derive increased value from radiation delivery systems that rotate rapidly around the subject (e.g., a patient). The rapid rotation enables 3-D X-ray and tomosynthesis imaging to be performed with better timing resolution, which may allow greater consistency between tomographic projections. Multi-view 2D imaging may also be performed with shorter delays between projection acquisitions, which may improve the spatiotemporal consistency between projections. Present systems capable of multiple fast rotations may employ binary (1-D) collimators since 2-D MLCs are too slow to modulate the beam as required to take advantage of a fast rotation rate. If 2-D MLCs is used with present fast rotating systems, the duty cycle of radiation delivery may be low. In some embodiments, treatment times may increase, and patient throughput may decrease. The present teachings describe how treatments can be planned to increase the treatment duty cycle by superimposing 2-D treatment fields over multiple rotations. Current fast rotating systems that use binary (1-D) MLCs treat on an axial slice-by-slice basis, advancing the patient couch as the system rotates, without superimposing fields across multiple rotations. The present teachings allow increased flexibility with respect to the order of delivery of the radiation segments, since the order of the planned rotations may be altered based on considerations including, such as: (1) respiration phase or other physiological/anatomical state, (2) organ positions as sensed using imaging or otherwise, (3) measured or estimated cumulative dose delivered, and (4) the need to perform image acquisition to update images/views of the subject.

The present disclosure provides embodiments of systems for simultaneous imaging and radiation therapy. In the context of a pulsed, and variable-duty cycle radiation delivery and imaging system (e.g., the radiation system 100), the term "simultaneous" requires disambiguation. Linear accelerator sources (e.g., the first radiation source 114 and the second radiation source 113) may typically produce pulses with duty cycles (e.g., a ratio between an on-period and an off-period) of the order of 1:1000. For the vast majority of time that the beam is in an "on" state, no radiation may be being produced. It is possible to image during the off-period. Such imaging may be still regarded as occurring simultaneously with the treatment. This is because the treatment has already commenced, and may continue within a short time period. There may be periods of the order 1-10,000 ms, between parts of the treatment delivery, where the treatment source is switched off or collimated off. Imaging that occurs during this time, as well as imaging that occurs while the treatment beam is on, may be both regarded as imaging that is simultaneous with treatment. In contrast, imaging that occurs after the treatment beam has been off (i.e., is not imparting substantial dose to the patient) for more than a complete system rotation, and imaging that occurs more than 10 s after the treatment beam has been turned off, may be not regarded, for the purposes of the teachings contained herein, as imaging that is simultaneous with the treatment.

It should be noted that the terms "first," "second," "third," "fourth," etc. are only for ease of description and do not represent a particular order or name. For example, a first rotation of the plurality of rotations may not necessarily mean the first executed rotation. As another example, a second rotation of the plurality of rotations may not necessarily mean the second executed rotation.

Having thus described the basic concepts, it may be rather apparent to those skilled in the art after reading this detailed disclosure that the foregoing detailed disclosure is intended to be presented by way of example only and is not limiting. Various alterations, improvements, and modifications may occur and are intended to those skilled in the art, though not expressly stated herein. These alterations, improvements, and modifications are intended to be suggested by this disclosure, and are within the spirit and scope of the exemplary embodiments of this disclosure.

Moreover, certain terminology has been used to describe embodiments of the present disclosure. For example, the terms "one embodiment," "an embodiment," and/or "some embodiments" mean that a particular feature, structure or characteristic described in connection with the embodiment is included in at least one embodiment of the present disclosure. Therefore, it is emphasized and should be appreciated that two or more references to "an embodiment" or "one embodiment" or "an alternative embodiment" in various portions of this specification are not necessarily all referring to the same embodiment. Furthermore, the particular features, structures or characteristics may be combined as suitable in one or more embodiments of the present disclosure.

Further, it will be appreciated by one skilled in the art, aspects of the present disclosure may be illustrated and described herein in any of a number of patentable classes or context including any new and useful process, machine, manufacture, or composition of matter, or any new and useful improvement thereof. Accordingly, aspects of the present disclosure may be implemented entirely hardware, entirely software (including firmware, resident software, micro-code, etc.) or combining software and hardware implementation that may all generally be referred to herein as a "unit," "module," or "system." Furthermore, aspects of the present disclosure may take the form of a computer program product embodied in one or more computer readable media having computer readable program code embodied thereon.

A non-transitory computer readable signal medium may include a propagated data signal with computer readable program code embodied therein, for example, in baseband or as part of a carrier wave. Such a propagated signal may take any of a variety of forms, including electro-magnetic, optical, or the like, or any suitable combination thereof. A computer readable signal medium may be any computer readable medium that is not a computer readable storage medium and that may communicate, propagate, or transport a program for use by or in connection with an instruction execution system, apparatus, or device. Program code embodied on a computer readable signal medium may be transmitted using any appropriate medium, including wireless, wireline, optical fiber cable, RF, or the like, or any suitable combination of the foregoing.

Computer program code for carrying out operations for aspects of the present disclosure may be written in any combination of one or more programming languages, including an object oriented programming language such as Java, Scala, Smalltalk, Eiffel, JADE, Emerald, C++, C#, VB. NET, Python or the like, conventional procedural programming languages, such as the "C" programming language, Visual Basic, Fortran 2003, Per, COBOL 2002, PHP, ABAP, dynamic programming languages such as Python, Ruby and Groovy, or other programming languages. The program code may execute entirely on the user's computer, partly on the user's computer, as a stand-alone software package, partly on the user's computer and partly on a remote computer or entirely on the remote computer or server. In the latter scenario, the remote computer may be connected to the user's computer through any type of network, including a local area network (LAN) or a wide area network (WAN), or the connection may be made to an external computer (for example, through the Internet using an Internet Service Provider) or in a cloud computing environment or offered as a service such as a Software as a Service (SaaS).

Furthermore, the recited order of processing elements or sequences, or the use of numbers, letters, or other designations therefore, is not intended to limit the claimed processes and methods to any order except as may be specified in the claims. Although the above disclosure discusses through various examples what is currently considered to be a variety of useful embodiments of the disclosure, it is to be understood that such detail is solely for that purpose, and that the appended claims are not limited to the disclosed embodiments, but, on the contrary, are intended to cover modifications and equivalent arrangements that are within the spirit and scope of the disclosed embodiments. For example, although the implementation of various components described above may be embodied in a hardware device, it may also be implemented as a software only solution, e.g., an installation on an existing server or mobile device.

Similarly, it should be appreciated that in the foregoing description of embodiments of the present disclosure, various features are sometimes grouped together in a single embodiment, figure, or description thereof for the purpose of streamlining the disclosure aiding in the understanding of one or more of the various inventive embodiments. This method of disclosure, however, is not to be interpreted as reflecting an intention that the claimed object matter requires more features than are expressly recited in each claim. Rather, inventive embodiments lie in less than all features of a single foregoing disclosed embodiment.

In some embodiments, the numbers expressing quantities, properties, and so forth, used to describe and claim certain embodiments of the application are to be understood as being modified in some instances by the term "about," "approximate," or "substantially." For example, "about," "approximate," or "substantially" may indicate ±20% variation of the value it describes, unless otherwise stated. Accordingly, in some embodiments, the numerical parameters set forth in the written description and attached claims are approximations that may vary depending upon the desired properties sought to be obtained by a particular embodiment. In some embodiments, the numerical parameters should be construed in light of the number of reported significant digits and by applying ordinary rounding techniques. Notwithstanding that the numerical ranges and parameters setting forth the broad scope of some embodiments of the application are approximations, the numerical values set forth in the specific examples are reported as precisely as practicable.

Each of the patents, patent applications, publications of patent applications, and other material, such as articles, books, specifications, publications, documents, things, and/or the like, referenced herein is hereby incorporated herein by this reference in its entirety for all purposes, excepting any prosecution file history associated with same, any of same that is inconsistent with or in conflict with the present document, or any of same that may have a limiting affect as to the broadest scope of the claims now or later associated with the present document. By way of example, should there be any inconsistency or conflict between the description, definition, and/or the use of a term associated with any of the incorporated material and that associated with the present document, the description, definition, and/or the use of the term in the present document shall prevail.

In closing, it is to be understood that the embodiments of the application disclosed herein are illustrative of the principles of the embodiments of the application. Other modifications that may be employed may be within the scope of the application. Thus, by way of example, but not of limitation, alternative configurations of the embodiments of the application may be utilized in accordance with the teachings herein. Accordingly, embodiments of the present application are not limited to that precisely as shown and described.

What is claimed is:

1. A method implemented on at least one machine each of which has at least one processor and at least one storage device for determining a radiation treatment plan, the method comprising:
   determining a set of one or more optimization goals for radiation delivery by a therapeutic radiation delivery apparatus;
   determining a plurality of radiation segments by iteratively optimizing a dose distribution relative to the set of one or more optimization goals,
   the determining the plurality of radiation segments by iteratively optimizing the dose distribution relative to the set of one or more optimization goals comprising:
      determining a plurality of sections of a rotational movement of a radiation source of the therapeutic radiation delivery apparatus;

determining the plurality of radiation segments based on the plurality of sections by iteratively optimizing a dose distribution relative to the set of one or more optimization goals, comprising:
  for each section, determining a fluence map by iteratively optimizing the dose distribution relative to the set of one or more optimization goals, the fluence map corresponding to a plurality of angles within an angle range of the each section;
  decomposing the plurality of fluence maps;
  determining the plurality of radiation segments based on the plurality of decomposed fluence maps; or
the determining the plurality of radiation segments by iteratively optimizing the dose distribution relative to the set of one or more optimization goals comprising:
  determining, based on the plurality of sections, the plurality of radiation segments by optimizing, according to direct aperture optimization, angle ranges, segment shapes, and segment MU values of the plurality of radiation segments in an iterative optimizing operation;
determining a sequence of the plurality of radiation segments for radiation delivery to obtain a delivery trajectory of the radiation source of the therapeutic radiation delivery apparatus;
determining a radiation treatment plan based on the plurality of sequential radiation segments for radiation delivery and the delivery trajectory of the radiation source of the therapeutic radiation delivery apparatus; and
delivering a radiation beam to a target volume based on the radiation treatment plan.

2. The method of claim 1, wherein determining a plurality of sections comprises:
  segmenting a rotation range of the rotational movement randomly or uniformly to obtain the plurality of sections.

3. The method of claim 1, wherein determining a plurality of sections comprises:
  segmenting a rotation range of the rotational movement based on one or more constraints associated with the therapeutic radiation delivery apparatus to obtain the plurality of sections.

4. The method of claim 1, wherein determining a plurality of sections comprises:
  segmenting a rotation range of the rotational movement based on the set of one or more optimization goals to obtain the plurality of sections.

5. The method of claim 1, wherein determining a plurality of radiation segments by iteratively optimizing a dose distribution relative to the set of one or more optimization goals comprises:
  determining a segment count of the plurality of radiation segments, an angle range of each of the plurality of radiation segments, one or more segment shapes of each of the plurality of radiation segments, one or more segment MU rates of each of the plurality of radiation segments, and/or one or more segment MU values of each of the plurality of radiation segments.

6. The method of claim 1, wherein iteratively optimizing a dose distribution relative to the set of one or more optimization goals comprises:
  iteratively optimizing the dose distribution relative to the set of one or more optimization goals based on one or more constraints associated with the therapeutic radiation delivery apparatus.

7. The method of claim 1, wherein determining a sequence of the plurality of radiation segments for radiation delivery to obtain a delivery trajectory of a radiation source of the therapeutic radiation delivery apparatus comprises:
  determining the sequence of the plurality of radiation segments based on the plurality of radiation segments and one or more constraints associated with the therapeutic radiation delivery apparatus.

8. The method of claim 1, wherein iteratively optimizing a dose distribution relative to the set of one or more optimization goals comprises:
  in at least one iteration,
    determining a plurality of sub-segments of at least one radiation segment of the plurality of radiation segments based on one or more control points;
    determining a collimator angle of an MLC of the therapeutic radiation delivery apparatus and a segment shape for each control point of the one or more control points; and
    determining an MU value for each sub-segment of the plurality of sub-segments;
  iteratively optimizing the dose distribution relative to the set of one or more optimization goals based on the plurality of sub-segments and the plurality of radiation segments excluding the at least one radiation segment.

9. The method of claim 1, wherein the delivery trajectory includes a plurality of rotations.

10. The method of claim 9, wherein at least one portion of a segment MU value of a radiation segment of the plurality of radiation segments is distributed in at least two rotations of the plurality of rotations.

11. The method of claim 9, wherein a first rotation of the plurality of rotations includes one or more first radiation segments, a second rotation of the plurality of rotations includes one or more second radiation segments.

12. The method of claim 11, wherein at least one first radiation segment of the first rotation is different from at least one second radiation segment of the second rotation.

13. The method of claim 11, wherein one of the one or more first radiation segments and one of the one or more second radiation segments have a same angle range, a same segment shape, a same segment MU rate, and/or a same segment MU value.

14. The method of claim 1, further comprising:
  obtaining one or more imaging protocols that are to be executed during radiation therapy, an execution interval of the one or more imaging protocols, and/or an execution sequence of the one or more imaging protocols, and iteratively optimizing a dose distribution relative to the set of one or more optimization goals comprises:
  iteratively optimizing the dose distribution relative to the set of one or more optimization goals based on one or more constraints associated with the therapeutic radiation delivery apparatus and the one or more imaging protocols.

15. The method of claim 14, further comprising:
  adjusting the radiation treatment plan based on the one or more imaging protocols by at least one of
  adjusting an angle range of a radiation segment,
  adjusting a segment shape of a radiation segment,
  adjusting a segment MU value of a radiation segment,
  adjusting a segment MU rate of a radiation segment,
  adjusting a sub-segment of a radiation segment,
  adjusting the sequence of the plurality of radiation segments and/or a plurality of sub-segments of the plurality of radiation segments,
  increasing a time for radiation therapy, delaying a time for radiation delivery in a radiation segment, adding an imaging plan associated with the one or more imaging protocols to the radiation treatment plan, or adding one or more rotations including no radiation delivery between a first radiation segment of the plurality of radiation segments and a second radiation segment of the plurality of radiation segments.

16. A system comprising:

at least one storage device storing a set of instructions; and at least one processor in communication with the at least one storage device, wherein when executing the set of instructions, the at least one processor is configured to cause the system to:

determine a set of one or more optimization goals for radiation delivery by a therapeutic radiation delivery apparatus;

determine a plurality of radiation segments by iteratively optimizing a dose distribution relative to the set of one or more optimization goals, wherein to determine the plurality of radiation segments by iteratively optimizing the dose distribution relative to the set of one or more optimization goals, the at least one processor is configured to cause the system to:

determine a plurality of sections of a rotational movement of a radiation source of the therapeutic radiation delivery apparatus; and determine the plurality of radiation segments based on the plurality of sections by iteratively optimizing a dose distribution relative to the set of one or more optimization goals, wherein to determine the plurality of radiation segments based on the plurality of sections by iteratively optimizing a dose distribution relative to the set of one or more optimization goals, the at least one processor is configured to cause the system to:

for each section, determine a fluence map by iteratively optimizing the dose distribution relative to the set of one or more optimization goals, the fluence map corresponding to a plurality of angles within an angle range of the each section;

decompose the plurality of fluence maps;

determine the plurality of radiation segments based on the plurality of decomposed fluence maps; or wherein to determine the plurality of radiation segments by iteratively optimizing the dose distribution relative to the set of one or more optimization goals, the at least one processor is configured to cause the system to:

determine, based on the plurality of sections, the plurality of radiation segments by optimizing, according to direct aperture optimization, angle ranges, segment shapes, and segment MU values of the plurality of radiation segments in an iterative optimizing operation;

determine a sequence of the plurality of radiation segments for radiation delivery to obtain a delivery trajectory of the radiation source of the therapeutic radiation delivery apparatus;

determine a radiation treatment plan based on the plurality of sequential radiation segments for radiation delivery and the delivery trajectory of the radiation source of the therapeutic radiation delivery apparatus; and deliver a radiation beam to a target volume based on the radiation treatment plan.

17. A non-transitory computer readable medium, comprising at least one set of instructions, wherein when executed by at least one processor of a computing device, the at least one set of instructions cause the at least one processor to effectuate a method comprising:

determining a set of one or more optimization goals for radiation delivery by a therapeutic radiation delivery apparatus;

determining a plurality of radiation segments by iteratively optimizing a dose distribution relative to the set of one or more optimization goals, the determining the plurality of radiation segments by iteratively optimizing the dose distribution relative to the set of one or more optimization goals comprising:

determining a plurality of sections of a rotational movement of a radiation source of the therapeutic radiation delivery apparatus;

determining the plurality of radiation segments based on the plurality of sections by iteratively optimizing a dose distribution relative to the set of one or more optimization goals, comprising:

for each section, determining a fluence map by iteratively optimizing the dose distribution relative to the set of one or more optimization goals, the fluence map corresponding to a plurality of angles within an angle range of the each section;

decomposing the plurality of fluence maps;

determining the plurality of radiation segments based on the plurality of decomposed fluence maps; or the determining the plurality of radiation segments by iteratively optimizing the dose distribution relative to the set of one or more optimization goals comprising:

determining, based on the plurality of sections, the plurality of radiation segments by optimizing, according to direct aperture optimization, angle ranges, segment shapes, and segment MU values of the plurality of radiation segments in an iterative optimizing operation;

determining a sequence of the plurality of radiation segments for radiation delivery to obtain a delivery trajectory of the radiation source of the therapeutic radiation delivery apparatus;

determining a radiation treatment plan based on the plurality of sequential radiation segments for radiation delivery and the delivery trajectory of the radiation source of the therapeutic radiation delivery apparatus; and delivering a radiation beam to a target volume based on the radiation treatment plan.

* * * * *